United States Patent
To et al.

(10) Patent No.: US 8,007,506 B2
(45) Date of Patent: *Aug. 30, 2011

(54) ATHERECTOMY DEVICES AND METHODS

(75) Inventors: John To, Newark, CA (US);
Christopher James Danek, San Carlos, CA (US)

(73) Assignee: Atheromed, Inc., Menlo Park, CA (US)

( * ) Notice: Subject to any disclaimer, the term of this patent is extended or adjusted under 35 U.S.C. 154(b) by 1058 days.

This patent is subject to a terminal disclaimer.

(21) Appl. No.: 11/551,203

(22) Filed: Oct. 19, 2006

(65) Prior Publication Data
US 2008/0004646 A1 Jan. 3, 2008

Related U.S. Application Data

(60) Provisional application No. 60/806,417, filed on Jun. 30, 2006, provisional application No. 60/820,475, filed on Jul. 26, 2006.

(51) Int. Cl.
*A61B 17/22* (2006.01)
(52) U.S. Cl. ........................................... 606/159
(58) Field of Classification Search ............... 606/108, 606/158, 159, 167, 170, 171, 180, 198; 128/898
See application file for complete search history.

(56) References Cited

U.S. PATENT DOCUMENTS

| | | | |
|---|---|---|---|
| 4,167,944 A | 9/1979 | Banko | |
| 4,445,509 A | 5/1984 | Auth | |
| 4,598,710 A | 7/1986 | Kleinberg et al. | |
| 4,631,052 A | 12/1986 | Kensey | |
| 4,669,469 A | 6/1987 | Gifford, III et al. | |
| 4,690,140 A | 9/1987 | Mecca | |
| 4,696,667 A | 9/1987 | Masch | |
| 4,770,652 A | 9/1988 | Mahurkar | |
| 4,790,812 A | 12/1988 | Hawkins, Jr. et al. | |
| 4,804,364 A | 2/1989 | Dieras et al. | |
| 4,808,153 A | 2/1989 | Parisi | |
| 4,844,064 A | 7/1989 | Thimsen et al. | |
| 4,857,045 A | 8/1989 | Rydell | |
| 4,857,046 A | 8/1989 | Stevens et al. | |
| 4,886,490 A * | 12/1989 | Shiber | 604/22 |
| 4,887,599 A | 12/1989 | Muller | |
| 4,894,051 A | 1/1990 | Shiber | |
| 4,950,277 A | 8/1990 | Farr | |
| 4,994,067 A * | 2/1991 | Summers | 606/159 |

(Continued)

FOREIGN PATENT DOCUMENTS
EP 0817594 6/2002

(Continued)

OTHER PUBLICATIONS

Ikeno, et al., "Initial Experience with the Novel 6 Fr-Compatible System for Debulking De Novo Coronary Arterial Lesions", vol. 62; pp. 308-317, 2004, Catheterization and Cardiovasbular Interventions.

(Continued)

*Primary Examiner* — Tuan Nguyen
(74) *Attorney, Agent, or Firm* — Ryan Kromholz & Manion, S.C.

(57) ABSTRACT

The devices and methods generally relate to treatment of occluded body lumens. In particular, the present devices and method relate to removal of the occluding material from the blood vessels as well as other body lumens.

6 Claims, 14 Drawing Sheets

U.S. PATENT DOCUMENTS

| | | | |
|---|---|---|---|
| 5,074,841 A | 12/1991 | Ademovic et al. | |
| 5,100,426 A | 3/1992 | Nixon | |
| 5,114,399 A * | 5/1992 | Kovalcheck | 604/22 |
| 5,231,989 A * | 8/1993 | Middleman et al. | 600/434 |
| 5,242,461 A | 9/1993 | Kortenbach et al. | |
| 5,267,955 A | 12/1993 | Hanson | |
| 5,282,813 A | 2/1994 | Redha | |
| 5,312,427 A | 5/1994 | Shturman | |
| 5,314,438 A | 5/1994 | Shturman | |
| 5,320,635 A | 6/1994 | Smith | |
| 5,356,418 A | 10/1994 | Shturman | |
| 5,358,472 A | 10/1994 | Vance et al. | |
| 5,360,432 A | 11/1994 | Shturman | |
| 5,370,609 A | 12/1994 | Drasler et al. | |
| 5,372,587 A | 12/1994 | Hammerslag et al. | |
| 5,409,454 A | 4/1995 | Fischell et al. | |
| 5,423,799 A | 6/1995 | Shiu | |
| 5,429,604 A | 7/1995 | Hammersmarck et al. | |
| 5,429,617 A | 7/1995 | Hammersmarck et al. | |
| 5,431,173 A | 7/1995 | Chin et al. | |
| 5,456,680 A | 10/1995 | Taylor et al. | |
| 5,474,532 A | 12/1995 | Steppe | |
| 5,489,291 A | 2/1996 | Wiley | |
| 5,501,653 A | 3/1996 | Chin | |
| 5,520,609 A | 5/1996 | Moll et al. | |
| 5,529,580 A | 6/1996 | Kusunoki et al. | |
| 5,540,706 A | 7/1996 | Aust et al. | |
| 5,554,163 A | 9/1996 | Shturman | |
| 5,556,408 A | 9/1996 | Farhat | |
| 5,584,843 A | 12/1996 | Wulfman et al. | |
| 5,618,294 A | 4/1997 | Aust et al. | |
| 5,626,562 A * | 5/1997 | Castro | 604/508 |
| 5,632,755 A | 5/1997 | Nordgren et al. | |
| 5,634,883 A | 6/1997 | Chin et al. | |
| 5,643,178 A | 7/1997 | Moll et al. | |
| 5,643,251 A | 7/1997 | Hillsman et al. | |
| 5,643,297 A | 7/1997 | Nordgren et al. | |
| 5,643,298 A | 7/1997 | Nordgren et al. | |
| 5,649,941 A | 7/1997 | Lary | |
| 5,665,062 A | 9/1997 | Houser | |
| 5,665,098 A | 9/1997 | Kelly et al. | |
| 5,669,926 A | 9/1997 | Aust et al. | |
| 5,690,634 A | 11/1997 | Muller et al. | |
| 5,695,506 A | 12/1997 | Pike et al. | |
| 5,716,327 A | 2/1998 | Warner et al. | |
| 5,725,543 A | 3/1998 | Redha | |
| 5,728,129 A * | 3/1998 | Summers | 606/170 |
| 5,733,297 A | 3/1998 | Wang | |
| 5,743,456 A | 4/1998 | Jones et al. | |
| 5,746,758 A | 5/1998 | Nordgren et al. | |
| 5,755,731 A | 5/1998 | Grinberg | |
| 5,766,196 A | 6/1998 | Griffiths | |
| 5,820,592 A | 10/1998 | Hammerslag | |
| 5,843,103 A | 12/1998 | Wulfman | |
| 5,851,208 A | 12/1998 | Trott | |
| 5,851,212 A | 12/1998 | Zirps et al. | |
| 5,873,882 A | 2/1999 | Straub et al. | |
| 5,876,414 A | 3/1999 | Straub | |
| 5,882,329 A | 3/1999 | Patterson et al. | |
| 5,895,399 A | 4/1999 | Barbut et al. | |
| 5,897,566 A | 4/1999 | Shturman et al. | |
| 5,902,263 A | 5/1999 | Patterson et al. | |
| 5,902,313 A | 5/1999 | Redha | |
| 5,941,869 A | 8/1999 | Patterson et al. | |
| 5,941,893 A | 8/1999 | Saadat | |
| 6,001,112 A | 12/1999 | Taylor | |
| 6,015,420 A * | 1/2000 | Wulfman et al. | 606/168 |
| 6,027,514 A | 2/2000 | Stine et al. | |
| 6,042,593 A | 3/2000 | Starz et al. | |
| 6,053,923 A | 4/2000 | Veca et al. | |
| 6,066,153 A | 5/2000 | Lev | |
| 6,080,170 A * | 6/2000 | Nash et al. | 606/159 |
| 6,090,118 A | 7/2000 | McGuckin, Jr. | |
| 6,132,444 A | 10/2000 | Shturman et al. | |
| 6,139,557 A | 10/2000 | Passafaro et al. | |
| 6,142,955 A | 11/2000 | Farascioni et al. | |
| 6,146,395 A | 11/2000 | Kanz et al. | |
| 6,152,938 A | 11/2000 | Curry | |
| 6,156,046 A | 12/2000 | Passafaro et al. | |
| 6,165,209 A | 12/2000 | Patterson et al. | |
| 6,206,898 B1 | 3/2001 | Honeycutt et al. | |
| 6,237,405 B1 | 5/2001 | Leslie | |
| 6,238,405 B1 | 5/2001 | Findlay, III et al. | |
| 6,241,744 B1 | 6/2001 | Imran et al. | |
| 6,258,098 B1 | 7/2001 | Taylor et al. | |
| 6,264,630 B1 | 7/2001 | Mickley et al. | |
| 6,299,622 B1 | 10/2001 | Snow et al. | |
| 6,319,242 B1 | 11/2001 | Patterson et al. | |
| 6,355,027 B1 | 3/2002 | Le et al. | |
| 6,371,928 B1 | 4/2002 | Mcfann et al. | |
| 6,406,442 B1 | 6/2002 | McFann et al. | |
| 6,451,036 B1 | 9/2002 | Heitzmann et al. | |
| 6,454,779 B1 | 9/2002 | Taylor | |
| 6,482,215 B1 | 11/2002 | Shiber | |
| 6,482,217 B1 | 11/2002 | Pintor et al. | |
| 6,494,890 B1 | 12/2002 | Shturman et al. | |
| 6,497,711 B1 | 12/2002 | Plaia et al. | |
| 6,554,846 B2 | 4/2003 | Hamilton et al. | |
| 6,562,049 B1 | 5/2003 | Norlander et al. | |
| 6,565,588 B1 | 5/2003 | Clement et al. | |
| 6,572,630 B1 | 6/2003 | McGuckin, Jr. et al. | |
| 6,579,299 B2 | 6/2003 | McGuckin, Jr. et al. | |
| 6,596,005 B1 | 7/2003 | Drummond et al. | |
| 6,602,264 B1 | 8/2003 | McGuckin, Jr. | |
| 6,623,495 B2 | 9/2003 | Findlay, III et al. | |
| 6,629,953 B1 | 10/2003 | Boyd | |
| 6,638,233 B2 | 10/2003 | Corvi et al. | |
| 6,638,288 B1 | 10/2003 | Shturman | |
| RE38,335 E | 11/2003 | Aust et al. | |
| 6,656,195 B2 | 12/2003 | Peters et al. | |
| 6,666,854 B1 | 12/2003 | Lange | |
| 6,666,874 B2 | 12/2003 | Heitzmann et al. | |
| 6,702,830 B1 | 3/2004 | Demarais et al. | |
| 6,758,851 B2 | 7/2004 | Shiber | |
| 6,790,215 B2 | 9/2004 | Findlay, III et al. | |
| 6,800,085 B2 | 10/2004 | Selmon et al. | |
| 6,808,531 B2 | 10/2004 | Lafontaine et al. | |
| 6,818,001 B2 | 11/2004 | Wulfman et al. | |
| 6,818,002 B2 | 11/2004 | Shiber | |
| 6,830,577 B2 | 12/2004 | Nash et al. | |
| 6,843,797 B2 | 1/2005 | Nash et al. | |
| 6,860,235 B2 | 3/2005 | Anderson et al. | |
| 6,876,414 B2 | 4/2005 | Hara et al. | |
| 6,936,056 B2 | 8/2005 | Nash et al. | |
| 6,997,934 B2 | 2/2006 | Snow et al. | |
| 7,025,751 B2 | 4/2006 | Silva et al. | |
| 7,033,357 B2 | 4/2006 | Baxter et al. | |
| 7,037,316 B2 | 5/2006 | McGuckin, Jr. et al. | |
| RE39,152 E | 6/2006 | Aust et al. | |
| 7,172,610 B2 | 2/2007 | Heitzmann et al. | |
| 7,235,088 B2 * | 6/2007 | Pintor et al. | 606/159 |
| 7,344,546 B2 | 3/2008 | Wulfman et al. | |
| 7,399,307 B2 * | 7/2008 | Evans et al. | 606/194 |
| 7,479,147 B2 | 1/2009 | Honeycutt et al. | |
| 7,534,249 B2 | 5/2009 | Nash et al. | |
| 7,666,161 B2 | 2/2010 | Nash et al. | |
| 2002/0007190 A1 | 1/2002 | Wulfman et al. | |
| 2002/0077642 A1 | 6/2002 | Patel et al. | |
| 2002/0169467 A1 | 11/2002 | Heitzmann et al. | |
| 2002/0198550 A1 | 12/2002 | Nash et al. | |
| 2003/0018346 A1 | 1/2003 | Follmer et al. | |
| 2003/0078606 A1 | 4/2003 | Lafontaine et al. | |
| 2003/0100911 A1 | 5/2003 | Nash et al. | |
| 2003/0114869 A1 | 6/2003 | Nash et al. | |
| 2003/0125758 A1 | 7/2003 | Simpson et al. | |
| 2003/0139802 A1 | 7/2003 | Wulfman et al. | |
| 2004/0006358 A1 | 1/2004 | Wulfman et al. | |
| 2004/0087988 A1 | 5/2004 | Heitzmann et al. | |
| 2004/0097995 A1 | 5/2004 | Nash et al. | |
| 2004/0102772 A1 | 5/2004 | Baxter et al. | |
| 2004/0147934 A1 | 7/2004 | Kiester | |
| 2004/0167553 A1 | 8/2004 | Simpson et al. | |
| 2004/0167554 A1 | 8/2004 | Simpson et al. | |
| 2004/0181249 A1 | 9/2004 | Torrance et al. | |
| 2004/0220519 A1 | 11/2004 | Wulfman et al. | |
| 2004/0230212 A1 | 11/2004 | Wulfman | |
| 2004/0230213 A1 | 11/2004 | Wulfman et al. | |

| | | |
|---|---|---|
| 2004/0235611 A1 | 11/2004 | Nistal |
| 2004/0236312 A1 | 11/2004 | Nistal et al. |
| 2004/0243162 A1 | 12/2004 | Wulfman et al. |
| 2005/0004585 A1 | 1/2005 | Hall et al. |
| 2005/0020974 A1* | 1/2005 | Noriega et al. ............ 604/95.04 |
| 2005/0059990 A1 | 3/2005 | Ayala et al. |
| 2005/0113853 A1 | 5/2005 | Noriega et al. |
| 2005/0149084 A1 | 7/2005 | Kanz et al. |
| 2005/0177068 A1 | 8/2005 | Simpson |
| 2005/0197661 A1 | 9/2005 | Carrison et al. |
| 2005/0222519 A1 | 10/2005 | Simpson |
| 2005/0240146 A1 | 10/2005 | Nash et al. |
| 2006/0020327 A1 | 1/2006 | Lashinski et al. |
| 2006/0229646 A1* | 10/2006 | Sparks ......................... 606/159 |
| 2006/0239982 A1 | 10/2006 | Simpson |
| 2007/0225739 A1 | 9/2007 | Pintor et al. |
| 2007/0250000 A1 | 10/2007 | Magnin et al. |
| 2007/0282350 A1 | 12/2007 | Hernest |
| 2008/0045986 A1 | 2/2008 | To et al. |
| 2010/0174302 A1 | 7/2010 | Heitzmann et al. |

FOREIGN PATENT DOCUMENTS

| | | |
|---|---|---|
| EP | 0817595 | 6/2002 |
| EP | 1176915 | 10/2005 |
| EP | 1158910 | 10/2007 |
| EP | 1315460 | 12/2007 |
| EP | 1722694 | 5/2009 |
| EP | 1870044 | 7/2009 |
| WO | WO95/021576 | 8/1995 |
| WO | WO 00/54659 A1 | 9/2000 |

OTHER PUBLICATIONS

Kanjwal, et al., "Peripheral Arterial Disease—The Silent Killer", vol. 11, No. 4, pp. 225-232, 2004, JK-Practitioner.

Nakamura, et al., "Efficacy and Feasibility of Helixcision for Debulking Neointimal Hyperplasia for In-Stent Restenosis", vol. 57, pp. 460-466, 2002, Catheterization and Cardiovascular Interventions.

U.S. Appl. No. 12/871,780, filed Aug. 2010, Pintor.

Office Action mailed Oct. 12, 2010 in Related U.S. Appl. No. 12/215,854.

Office Action mailed Oct. 5, 2010 in Related U.S. Appl. No. 12/215,855.

Office Action mailed Oct. 5, 2010 in Related U.S. Appl. No. 12/215,752.

* cited by examiner

ATHERECTOMY DEVICES AND METHODS

CROSS-REFERENCE

This filing is a non-provisional of U.S. Provisional Application Ser. No. 60/806,417 entitled "Atherectomy Device" filed Jun. 30, 2006 and is a non-provisional of U.S. Provisional Application Ser. No. 60/820,475 entitled "Atherectomy Device" filed Jul. 26, 2006, the entirety of each of which are hereby incorporated reference.

BACKGROUND OF THE INVENTION

1. Field of the Invention

The devices and methods described below generally relate to treatment of occluded body lumens. In particular, the present devices and method relate to removal of the occluding material from the blood vessels as well as other body lumens.

2. Description of the Background Art

Atherosclerosis is a progressive disease. In this disease, lesions of the arteries are formed by accumulation of plaque and neointimal hyperplasia causing an obstruction of blood flow. Often plaque is friable and may dislodge naturally or during an endovascular procedure, leading to embolization of a downstream vessel.

Endovascular clearing procedures to reduce or remove the obstructions to restore luminal diameter allows for increased blood flow to normal levels are well known. Removing the plaque has the effect of removing diseased tissue and helps to reverse the disease. Maintaining luminal diameter for a period of time (several to many weeks) allows remodeling of the vessel from the previous pathological state to a more normal state. Finally, it is the goal of an endovascular therapy to prevent short term complications such as embolization or perforation of the vessel and long term complications such as ischemia from thrombosis or restenosis.

Various treatment modalities may help to accomplish treatment goals. In atherectomy, plaque is cut away, or excised. Various configurations are used including a rotating cylindrical shaver or a fluted cutter. The devices may include shielding by a housing for safety. The devices may also remove debris via trapping the debris in the catheter, in a downstream filter, or aspirating the debris. In some cases a burr may be used instead of a cutter, particularly to grind heavily calcified lesions into very small particle sizes. Aspiration may also be used with a burr-type atherectomy device.

Balloon angioplasty is another type of endovascular procedure. Balloon angioplasty expands and opens the artery by both displacing the plaque and compressing it. Balloon angioplasty is known to cause barotrauma to the vessel from the high pressures required to compress the plaque. This trauma leads to an unacceptably high rate of restenosis. Furthermore, this procedure may not be efficient for treatment of elastic-type plaque tissue, where such tissue can spring back to occlude the lumen.

When clearing such obstructions it is desirable to protect the vessel wall or wall of the body lumen being cleared and to debulk substantially all of a lesion. In additional cases, the procedure that clears obstructions may also be coupled with placement of an implant within the lumen. For example, it may be desirable to deploy a stent to maintain patency of a vessel for a period of time and/or to achieve local drug delivery by having the stent elute a drug or other bioactive substance.

On their own, stents fail to perform well in the peripheral vasculature for a variety of reasons. A stent with the necessary structural integrity to supply sufficient radial force to reopen the artery often does not perform well in the harsh mechanical environment of the peripheral vasculature. For example, the peripheral vasculature encounters a significant amount of compression, torsion, extension, and bending. Such an environment may lead to stent failure (strut cracking, stent crushing, etc.) that eventually compromises the ability of the stent to maintain lumen diameter over the long-term. On the other hand, a stent that is able to withstand the harsh mechanical aspects of the periphery often will not supply enough radial force to open the vessel satisfactorily. In many cases, medical practitioners desire the ability to combine endovascular clearing procedures with stenting.

Accordingly, a need remains for devices that allow for improved atherectomy devices that clear materials from body lumens (such as blood vessels) where the device includes features to allow for a safe, efficient and controlled fashion of shaving or grinding material within the body lumen.

SUMMARY OF THE INVENTION

Devices and methods described herein provide improved means of clearing obstructions within body lumens, especially the vasculature. The features of the devices and methods allow for controlled removal of occlusive materials. In some variations, the methods and devices also have features to convey the materials away from the operative site without the need to remove the devices from the body lumen. Additional aspects include controlled rates of tissue removal as well as other safety features to prevent accidental cutting of the lumen wall. Although the devices and methods described herein discuss removal of materials from a blood vessel, in certain cases the devices and methods have applicability in other body lumens as well. It should be noted that the variations and features of the devices described below may be incorporated selectively or in combination with a basic device configuration that includes a flexible body having a cutter head, where the cutter head includes a housing and a cutter, where the housing and cutter are able to rotate relative to each other. Variations include a cutter that rotates within the housing, a housing that rotates about the cutter, and combinations thereof.

One variation of the device described herein includes a device configured to remove material from body structures. The device may be a vascular device and have the required structure and configuration to navigate tortuous anatomy. Alternatively, the device may be a cutter that has features that are desired when used in other parts of the anatomy.

In any case, such a device may include a catheter body having a proximal end and a distal end, a cutter assembly located at the distal end of the catheter body, the cutter assembly comprising a housing having at least one opening and a cutter having at least one cutting surface configured to rotate relative to the housing, where movement between the housing opening and the cutting surface removes material located therebetween, a rotating shaft extending through the catheter body and coupled to the cutter, the shaft having a proximal end adapted to couple to a first rotating mechanism, and a deflecting member extending along the catheter body, such that movement of the deflecting member causes deflection of the cutter assembly relative to an axis of the catheter.

Variations of the deflecting member may include steerable sheaths adapted to deflect in shape. In some variations the steerable sheath may include a deflecting wire extending through a portion of the sheath, such that axial movement of the deflecting wire deflects the sheath. The deflecting wire can be affixed to the cutter assembly, to a portion of the catheter body that extends out of the deflecting sheath, or to other parts of the device as needed.

The deflecting member can also include a pre-shaped mandrel, or tube where such features are slidable within or relative to the device to produce movement of the cutting head relative to an axis of the device. The devices described herein may have any number of features that allow for locking the device after it is articulated. This feature provides a consistent diameter when sweeping or navigating through the anatomy.

As discussed herein, some variations of the devices have the ability to articulate. This articulation allows for steering the device to the target site as well as creating a sweeping motion of tissue removal. Accordingly, sheath used in the device can be rotatable about the catheter body, or about an axis of the catheter.

The devices described herein may have a cutter assembly having a portion of its housing having a curved surface and where the opening forms a plane across the curved surface such that as the cutting surface rotates across the opening, a portion of the cutting surface extends out of the housing through the opening. The cutter assembly may also have various other features as described below that improve the safety of the device as it is articulated while cutting. Furthermore the cutter may have a number of features to impel or drive cut tissue into the cutter assembly for eventual removal by one or more conveying members.

As noted, the devices described herein may have one or more conveying members that convey materials and/or fluids through the device. Such a feature is useful to remove cut tissue and debris from the site during the procedure. In some variations, the device may include multiple conveyors to deliver fluids and remove debris. However, the devices of the present invention may also have containers for use in capturing debris or other materials generated during the procedure.

Another feature for use with the inventions herein is the use of a burr rotatably coupled to a tip of the device. The burr can be useful to remove tissue that is otherwise not conducive to cutting with the cutter assembly.

In another variation, the invention may comprise a device having a straightening tube, with a straight distal portion, a catheter body having a proximal end and a distal end, the catheter body having a flexible section located towards the distal end, such that when located in the straight distal portion of the straightening tube the flexible section is less curved, a cutter assembly located at the distal end of the catheter body, the cutter assembly comprising a housing having at least one opening and a cutter having at least one cutting surface configured to rotate relative to the housing, where movement between the housing opening and the cutting surface removes material located therebetween, and a rotating shaft extending through the catheter body and coupled to the cutter, the torque shaft having a proximal end adapted to couple to a first rotating mechanism.

In such a case, placement of the straight distal portion over the catheter allows for manipulation of the degree of curvature of the catheter. This feature allows for steering of the device.

As described herein, such a device may have the ability to sweep over an arc to deliver a larger cutting diameter than the diameter of the cutter assembly.

The devices described herein may use a guidewire for advancement through the body. In such cases the devices will have guide-wire lumens located within or about the catheter. Alternatively, a guide-wire section may be affixed to a portion of the device.

Devices of the present invention typically include a torque shaft to deliver rotational movement to components in the cutter assembly. Alternatively, a torque shaft or other such assembly may be used to produce the sweeping action described herein. In any case, the torque shaft may include one or more lumens. Alternatively, the torque shaft may be a solid or hollow member. Variations of the torque shaft also include those aspects known in catheter-type devices such as counter-wound coils, stiffening members, etc. In some variations, the torque shaft may have the conveying member integrally formed about the exterior or an interior surface of the shaft. Alternatively, or in combination, the conveying member may be placed on (or within) the torque shaft as described herein.

The invention also includes various methods of debulking material within body structures. These structures include occluded blood vessels (whether partially or totally occluded), various organs, cavities within the body, or other body lumens.

In one variation a method includes inserting a catheter body having a cutter assembly within the blood vessel, rotating the cutter assembly to remove the material and form a first opening in the body lumen, deflecting the first cutter assembly relative to an axis of the catheter body, rotating the catheter body while rotating the cutter assembly to form a second opening in the body lumen where the second is larger than the first opening.

The methods may include the use of any of the devices or features of the devices described herein. In one variation, the methods include circulating fluid for contrast to better visualize the obstruction.

As noted herein, combinations of aspects of the devices, systems, and methods described herein may be combined as needed. Furthermore, combinations of the devices, systems and methods themselves are within the scope of the disclosure.

DESCRIPTION OF AN EMBODIMENT

Figure 1A:
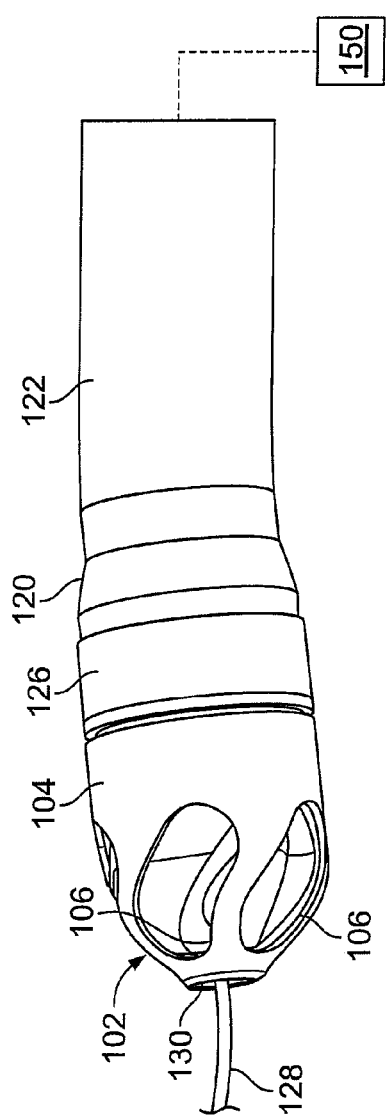
FIG. 1A illustrates an exemplary variation of a device according to the present invention.

FIG. 1A illustrates an exemplary variation of a device 100 according to the present invention. As shown the device 100 includes a cutter assembly 102 affixed to a catheter body 120. As shown, the catheter body may be optionally located within an outer sheath 122.

Figure 1B:
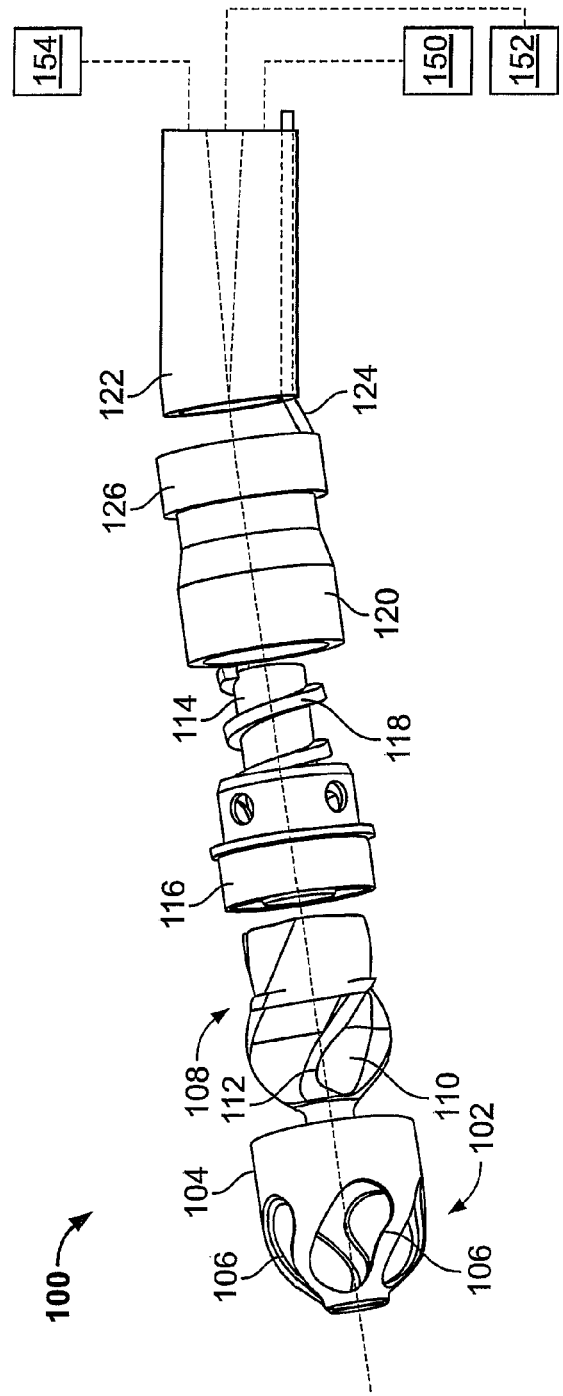
FIG. 1B shows an exploded view of the device of FIG. 1A.

FIG. 1B illustrates an exploded view of the device 100 of FIG. 1A. As shown, the cutter assembly 102 includes a housing 104 with a plurality of openings 106. A cutter 108 is located within the housing 104. The cutter 108 includes one or more flutes 110 each of which includes an edge or cutting surface 112. The cutter is coupled to a rotating mechanism 150. In this variation the rotating mechanism couples to the cutter via a torque shaft 114 that transmits rotational energy from the rotating mechanism 150 (e.g., an electric, pneumatic, fluid, gas, or other motor) to the cutter 108. Variations of the devices include use of a rotating mechanism 150 located entirely within the body of the device 100. In one variation, the rotating mechanism 150 may be outside of the surgical field (i.e., in a non-sterile zone) while a portion of the device (e.g., the torque shaft—not shown) extends outside of the surgical field and couples to the rotating mechanism. FIG. 1B also shows a variation of the device 100 as having a deflecting member 124 (the deflecting member may be a tendon, wire, tube, mandrel, or other such structure). As described in detail below, the devices 100 can have deflecting members to articulate the cutting head and allow for a sweeping motion of cutting.

In another variation, the device 100 may have a catheter body that comprises a soft or flexible portion. In one variation, this soft or flexible portion may be on a single side of the device 100 to allow flexure of the device 100 to articulate the cutting head. The flexure may be obtained with a curved sheath, mandrel, or other means as known to those skilled in the art.

The device 100 may also include a vacuum source or pump 152 to assist in evacuation of debris created by operation of the device. Any number of pumps or vacuum sources may be used in combination with the device. For example, a peristaltic pump may be used to drive materials from the device and into a waste container. FIG. 1B also shows the device 100 coupled to a fluid source 154. As with the rotating mechanism, the vacuum source and/or fluid source may be coupled to the device from outside the surgical field.

It may be advantageous to rotatably couple the torque shaft to the drive unit electromagnetically, without physical contact. For example, the torque shaft 114 can have magnetic poles installed at the proximal end, within a tubular structure that is attached to the sheath around the torque shaft. The stationary portion of the motor can be built into a handle that surrounds the tubular structure. This allows the continuous aspiration through the sheath without the use of high speed rotating seals.

Figure 1C:
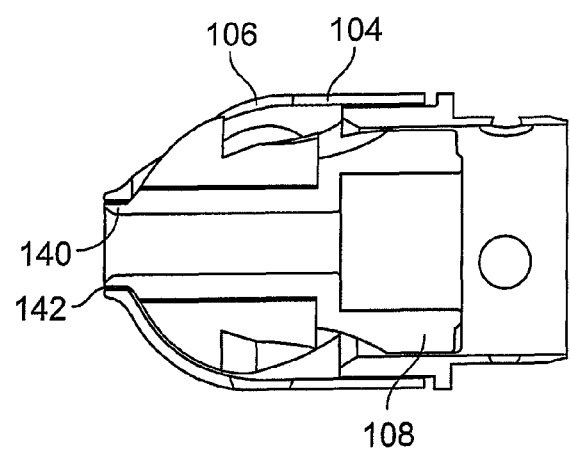
FIG. 1C shows a cross sectional view of the cutting assembly.

As shown in FIG. 1C, in certain variations, the housing 104 can have a distal nose with a center lumen 142 for receiving a mating piece 140 of the cutter 108. Such features assists in centering the cutter 104 concentrically inside the housing 104. The housing is preferably made of a strong, wear resistant material such as hardened steels, cobalt chromium, carbides or titanium alloys with or without wear resistant coatings like TiNi. In particular the use of coatings will allow the use of tool steels which, unless coated, do not have acceptable corrosion resistance and biocompatibility. As noted below, variations of the devices include the addition of a burr element (as described below) for grinding hard tissue such as calcified plaque.

The geometry of the cutter 108 and housing 104 can be used to tailor the desired degree of cutting. The housing 104 and orientation of the openings 106 can be used to limit the depth of cutting by the cutter 108. In addition, the distal end of the housing 104 may be domed shaped while the proximal end may have a cylindrical or other shape. For example, by creating larger windows 106 in the housing a larger portion of cutter 108 may be exposed and the rate of cutting increased (for a given rotation speed). By placing the cutting window 106 on a convex portion of the housing, the debulking effectiveness is much less sensitive to the alignment of the cutter housing to the lesion, than if the window were on the cylindrical portion of the housing. This is a key performance limitation of traditional directional atherectomy catheters. In addition, placement of the window on the convex portion of the housing creates a secant effect (as described below).

Figure 2A:
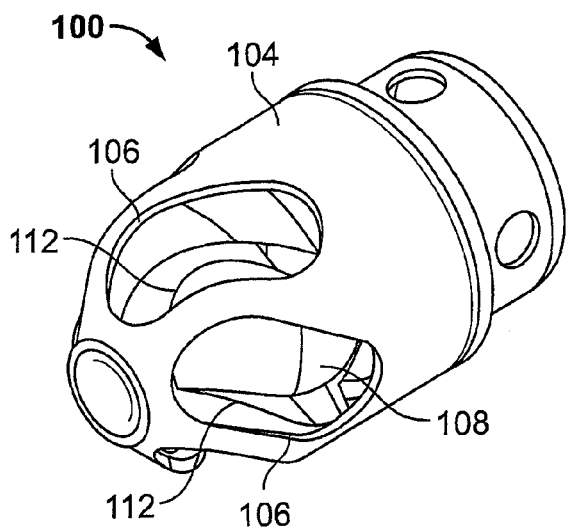
FIG. 2A shows alignment of the cutting edges with openings of a housing.

FIG. 2A illustrates an additional variation of the device 100 where the openings 106 may be helical slots that may or may not be aligned with the cutting surfaces 112 of the cutter 108. For aggressive cutting, the slots 106 and cutting edges 112 are aligned to maximize exposure of the tissue to cutting edges. In other words, the cutting edges 112 and openings 106 are in alignment so all cutting edges 112 are exposed at the same time to allow simultaneous cutting. Alternatively, alignment of the openings and edges 112 may be configured so that fewer than all the cutting edges 112 are exposed at the same time. For example, the alignment may be such that when one cutting edge 112 is exposed by an opening 106, the remaining cutting edges 112 are shielded within the housing 104. Variations of such a configuration allow for any number of cutting edges to be exposed at any given time.

However, to even out the torque profile of the device when cutting, the cutter 108 is configured such that the number edges/cutting surfaces 112 of the flutes 110 that are aligned with the housing openings 106 does not vary throughout the rotational cycle. This prevents the catheter from being overloaded with torque spikes and cyclic torque variations due to multiple cutting edges/flutes engaging with tissue in synchrony. In other words, the length of the cutting surface 112 exposed through the openings 106 of the housing 104 remains the same or constant.

Figure 2B:
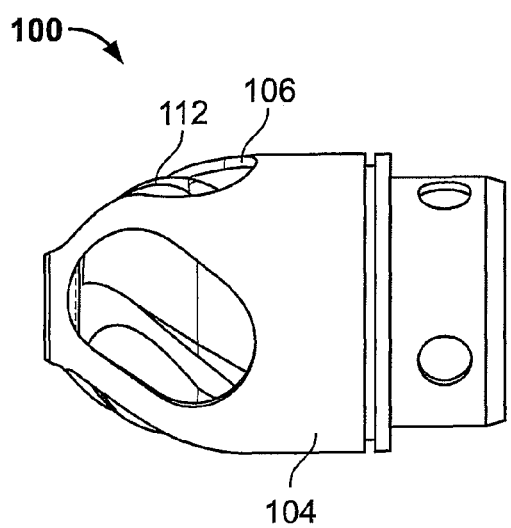
FIG. 2B shows a side view of the cutting assembly demonstrating the secant effect.

In the variation shown in FIG. 2B, the cutting surface 112 is configured to capture debris as it cuts. Typically, the device 100 may be designed with a secant effect. This effect allows for a positive tissue engagement by the cutter. As the cutter rotates through the opening, the cutting edge moves through an arc, where at the peak of the arc the cutting edge slightly protrudes above a plane of the opening. The amount of positive tissue engagement can be controlled through selection of the protrusion distance through appropriate design of the housing geometry (for example, by a combination of location and size of the window and radius of curvature of the housing). As shown, the cutting surface 112 extends out of the housing 104 through the window 106 as it rotates. This structure can also be designed to drive or impel the debris to the conveying member 118. In this case, the flutes 110 within the cutter 108 are helically slotted to remain in fluid communication with the conveying member 118. Variations of the device 100 can also include a vacuum source 152 fluidly coupled to the conveying member 118. In order to improve the impelling force generated by the cutters, variations of the cutter have helical flutes 110 and sharp cutting edges 112 that are parallel to each other and are wound from proximal to distal in the same sense as the rotation of the cutter. When the cutter rotates, it becomes an impeller causing tissue debris to move proximally for evacuation.

Figure 2C:
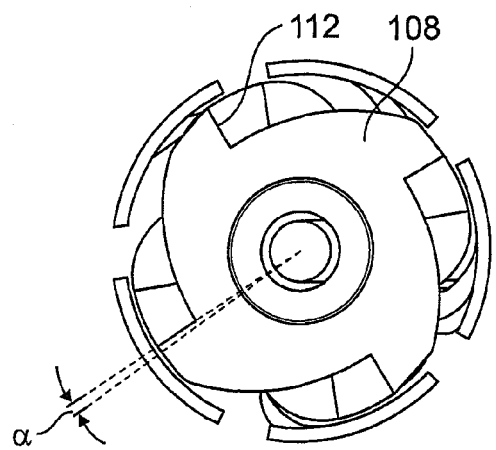
FIG. 2C illustrates a positive rake angle.

As shown in FIG. 2C, variations of the device may have cutting surfaces 112 with positive rake angles α—that is the cutting edge is pointed in the same direction as that of the cutter rotation. This configuration maximizes the effectiveness of the impelling and cutting action (by biting into tissue and avoiding tissue deflection). The cutter is preferably made of hard, wear-resistant material such as hardened tool or stainless steels, Tungsten carbide, cobalt chromium, or titanium alloys with or without wear resistant coatings as described above. However, any material commonly used for similar surgical applications may be employed for the cutter. The outer surfaces of the proximal end of the cutter 108 is typically blunt and is designed to bear against the housing 104. Typically, these surfaces should be parallel to the inner surface of the housing.

FIGS. 2A-2B also show a surface of the cutter 108 having a curved-in profile distally and is close to the housing 104 surface. Note that housing slots 106 with this curved profile allows the cutting edge 112 to protrude beyond the housing's outer surface. In other words, the openings 106 form a secant on the curved surface of the housing 104. Such a feature allows improved cutting of harder/stiffer material like calcified or stiff fibrous tissue where such tissue does not protrude into the housing 104.

By controlling the number of cutting edges 112 that are exposed through openings 106 in the housing 104, it is possible to control the relative amount of cutting engagement (both length of cutting and depth of cut, together which control the volume of tissue removed per unit rotation of the cutter). These features allow independent control of the maximum torque load imposed on the device 100. By carefully selecting the geometry of the flutes and or cutting edges 112 relative to the openings 106 in the housing, it is possible to further control the balance of torque. For example, the torque load imposed on the device is caused by the shearing of tissue when the cutter edge passes the rotationally distal edge of the window. If all cutter edges simultaneously shear, as for example when the number of housing windows is an even multiple of cutter edges, the torque varies cyclically with rotation of the cutter. By adjusting the number of cutters and windows so one is not an even multiple of the other (for example, by using 5 windows on the housing and 4 cutting edges on the cutter), it is possible to have a more uniform torque (tissue removal from shearing action) during each cycle of the cutter.

Figure 3:
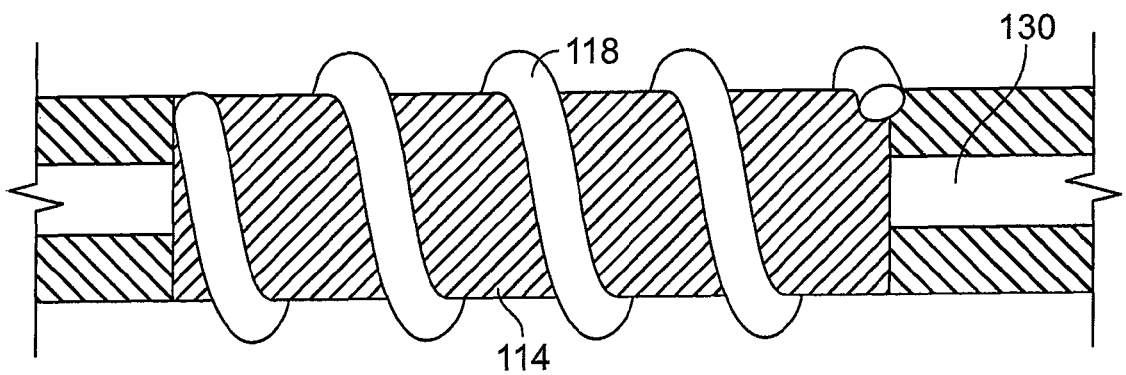
FIG. 3 shows a partial cross sectional view of a variation of a torque shaft having counter wound coils.

FIG. 3 shows a partial sectional view of a torque shaft 114 that is a set of counter-wound coils, with the outer coil wound at the proper (greater) pitch to form the conveying member 118. Winding the coils counter to each other automatically reinforces the torque shaft 114 during rotation. Alternatively, the torque shaft 114 may be made out of a rigid plastic, rendered flexible by incorporation of a conveying member 118. Although the shaft may be fabricated from any standard material, variations of the shaft include a metal braid embedded in polymer (PEBAX, polyurethane, polyethylene, fluoropolymers, parylene) or one or more metal coils embedded in a polymer such as PEBAX, polyurethane, polyethylene, fluoropolymers or parylene. These constructions maximize torsional strength and stiffness, as well as column strength for "pushability", and minimize bending stiffness for flexibility. Such features are important for navigation of the catheter through tortuous vessels. In the multi-coil construction, the inner coil should be wound in the same sense as that of the rotation so that it would tend to open up under torque resistance. This ensures that the guidewire lumen remain patent during rotation. The next coil should be wound opposite the inner to counter the expansion to keep the inner coil from binding up against the outer catheter tube.

FIG. 3 also shows a torque shaft 114 having a central lumen 130. Typically the lumen will be used to deliver a guidewire. In such cases, the central lumen may be coated with a lubricious material (such as a hydrophilic coating or Parylene) or made of a lubricious material such as PTFE to avoid binding with the guidewire. However, in some variations a guidewire section is affixed to a distal end of the housing. Moreover, the central lumen of the torque shaft 114 may also be used to deliver fluids to the operative site simultaneously with the guidewire or in place of the guidewire.

Figure 4A:
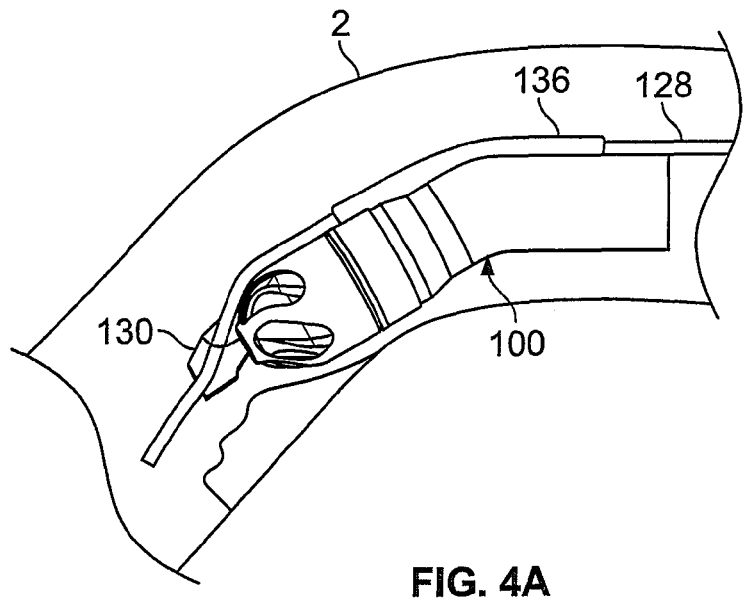
FIG. 4A shows a variation of a device configured for rapid exchange.

FIG. 4A illustrates a variation of a device 100 configured for rapid exchange. As shown, the device 100 includes a short passage, lumen, or other track 136 for the purpose of advancing the device 100 over a guidewire 128. However, the track 136 does not extend along the entire length of the device 100. Moreover, an additional portion of the track 136 may be located at a distal end of the catheter to center a guidewire 128.

This feature permits decoupling of the device 100 and guidewire 128 by merely pulling the guidewire 128 out of the track 136 (as opposed to needing to remove the guidewire 128 from the length of the device 136). One benefit of such a feature is that the guidewire 128 may remain close to the site while being decoupled from the device 100. Accordingly, the surgeon can advance additional devices over the guidewire and to the site in a rapid fashion. This configuration allows for quick separation of the catheter from the wire and introduction of another catheter over the wire since most of the wire is outside of the catheter.

Figure 4B:
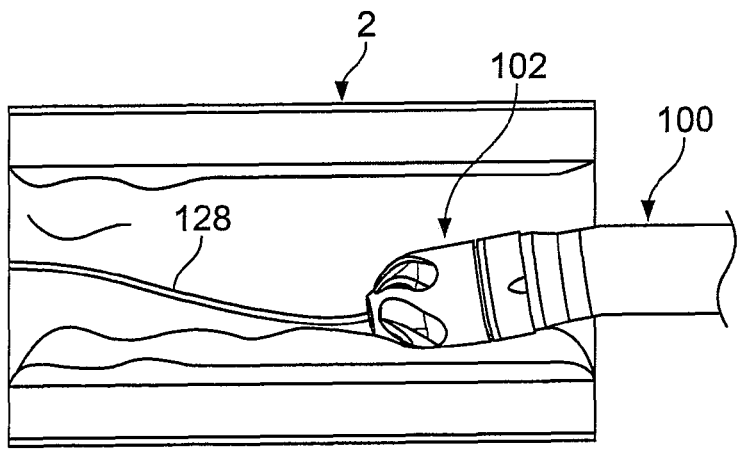
FIG. 4B illustrates an example of centering a tip of a cutting assembly over a guide wire.

As shown in FIG. 4B, centering the tip of the cutting assembly 102 over a guide wire 128 improves the control, access and positioning of the cutting assembly 102 relative to a body lumen or vessel 2. To accomplish this, the cutting assembly 102 can have a central lumen to accommodate a guide wire 128. Variations of the device 100 includes a central guide wire lumen runs the length of the catheter through all central components including the torque shaft and the cutter. As noted above, a guidewire 128 can be affixed to the housing 104 or other non-rotational component of the cutting assembly 102. In such a case, the guidewire 128 may preferably be a short segment that assists with navigation of the device through an occluded portion of a body lumen. However, the devices 100 can also operate without a guidewire since the head is steerable like a guidewire.

Figure 5A:
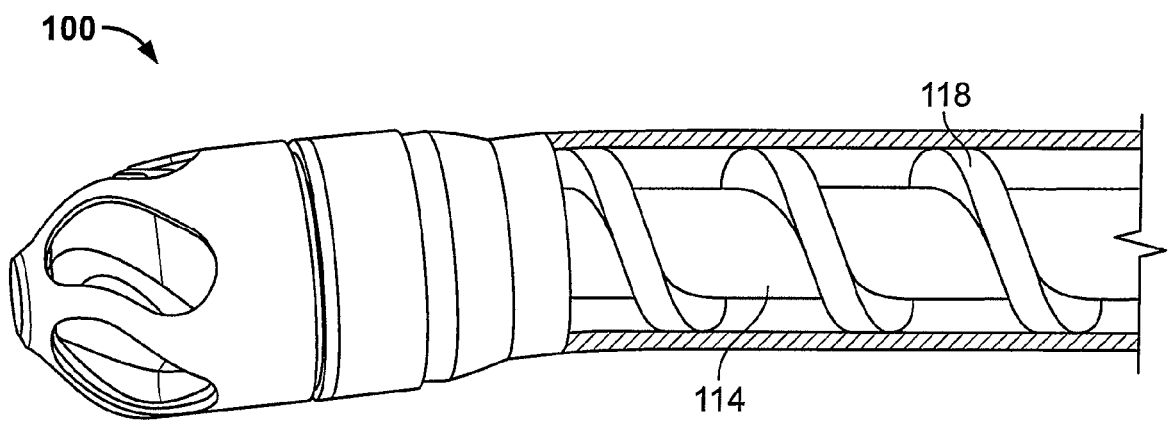
FIG. 5A shows a conveyor within the device.

FIG. 5A illustrates a partial cross-sectional view of the device 100. As shown, this variation of the device 100 includes a conveyor member 118 located within the device 100. The conveyor member 118 may be an auger type system or an Archimedes-type screw that conveys the debris and material generated during the procedure away from the operative site. In any case, the conveying member 118 will have a raised surface or blade that drives materials in a proximal direction away from the operative site. Such materials may be conveyed to a receptacle outside of the body or such materials may be stored within the device 100. In one variation, the torque shaft 114 and conveying member 118 extend along the length of the catheter.

Figure 5B:
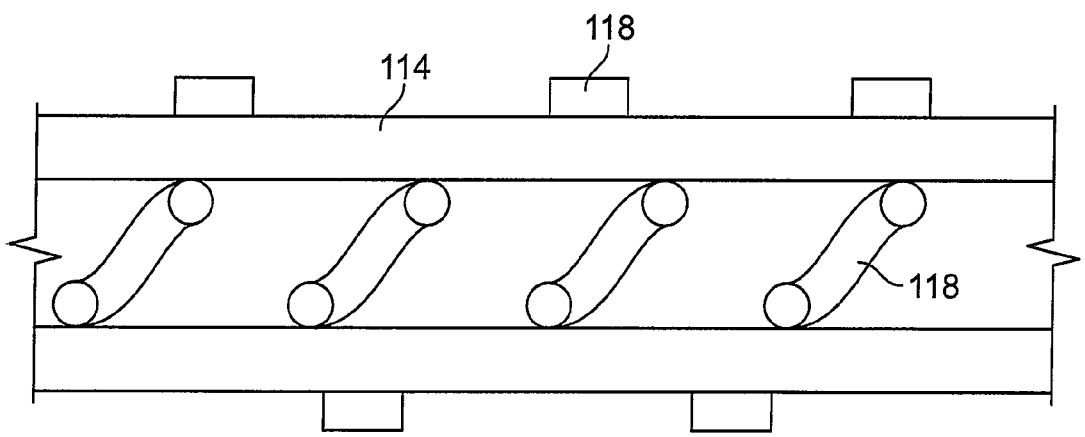
FIG. 5B shows a second conveyor within a torque shaft.

In some variations, the conveying member 118 may be integral to the shaft 114 (such as by cutting the conveying member 118 into the torque shaft 114 or by extruding the torque shaft 114 directly with a helical groove or protrusion. In an additional variation as shown in FIG. 5B, an additional conveying member 118 may be incorporated on an inside of the torque shaft, where the internal conveying member is wound opposite to that of the external conveying member 118. Such a configuration allows for aspiration and debris (via the external conveying member 118) and infusion (via the internal conveying member 118). Such a dual action can enhance the ability to excise and aspirate plaque by: (1) thinning the blood, whether by viscosity alone or with the addition of anti-coagulants such as heparin or warfarin (cumadin), (2) improving the pumpability (aspirability) of the excised plaque by converting it into a solid-liquid slurry that exhibits greater pumping efficiency, and (3) establishing a flow-controlled secondary method of trapping emboli that are not sheared directly into the housing, by establishing a local recirculation zone.

As noted above, the conveying member 118 can be wound in the same directional sense as the cutter 108 and in the same direction of rotation to effect aspiration of tissue debris. The impeller action of the cutter 108 moves the tissue debris from inside the housing 104 openings 106 into the torque shaft. The pitch of the cutting edges 112 maybe matched in to that of the conveying member 118 to further optimize aspiration. Alternatively, the pitch of the conveying member 118 may be changed to increase the speed at which material moves once it enters the conveying member 118. As discussed herein, debris can be evacuated outside the body by the conveying member 118 action along the length of the catheter and with or without supplement of the vacuum 152 pump connected to the catheter handle. Alternatively, the debris may be accumulated in a reservoir within the device.

The device may also include a ferrule 116, as shown in FIG. 1B, that permits coupling of the catheter body 120 to the cutter assembly 102. The ferrule 116 may serve as a bearing surface for rotation of the cutter 108 within the cutter assembly 102. In the illustrated variation, the torque shaft 114 rotates inside the outer catheter body 120 and ferrule 116 to rotate the cutter and pull or aspirate tissue debris in a proximal direction. The clearance between the catheter tube and conveying member 118, as well as the pitch and thread depth of the conveying member 118, are chosen to provide the desired pumping effectiveness.

In one variation of the device, the housing 104 is connected to the catheter body 120 via the ferrule 116 and thus is static. The cutter 108 rotates relative to the housing 104 so the cutting surface 112 on the cutter 108 cooperates with openings 106 on the housing 104 to shear or cleave tissue and trap the tissue inside the housing so that it can be evacuated in a proximal direction using the impeller action of the helical flutes and vacuum from the torque shaft.

The ferrule 116 can have a distal bearing surface to bear against the proximal surface of the cutter 108 and keeps the cutter axially stable in the housing 104. It can be rigidly bonded/linked to the housing 104 using solder, brazing, welding, adhesives (epoxy), swaging, crimped, press-fit, screwed on, snap-locked or otherwise affixed. As shown, the ferrule 116 can have holes or other rough features that allow for joining with the catheter body. While adhesives and heat fusing may be employed in the construction, such features are not required. Often adhesives are unreliable for a small surface contact and heat fusing can cause the tube to degrade. The use of a mechanical locking ring 126 allows the cutting assembly 102 to be short. Such a feature is important for maximizing the flexibility of the distal section of the catheter as it is required to navigate tortuosity in blood vessels.

In another aspect of the invention, devices 100 can be adapted to steer to remove materials that are located towards a side of the body passage. Such devices may include a deflecting member that permits adjusting the orientation or offset of the cutter assembly 102 relative to a central axis of the device. In FIG. 1B, the deflecting member comprises a sheath 122 with a deflecting member 124 (such as a tendon, wire, tube, mandrel, or other such structure.) However, as described herein, other variations are within the scope of the device.

Figure 6A:
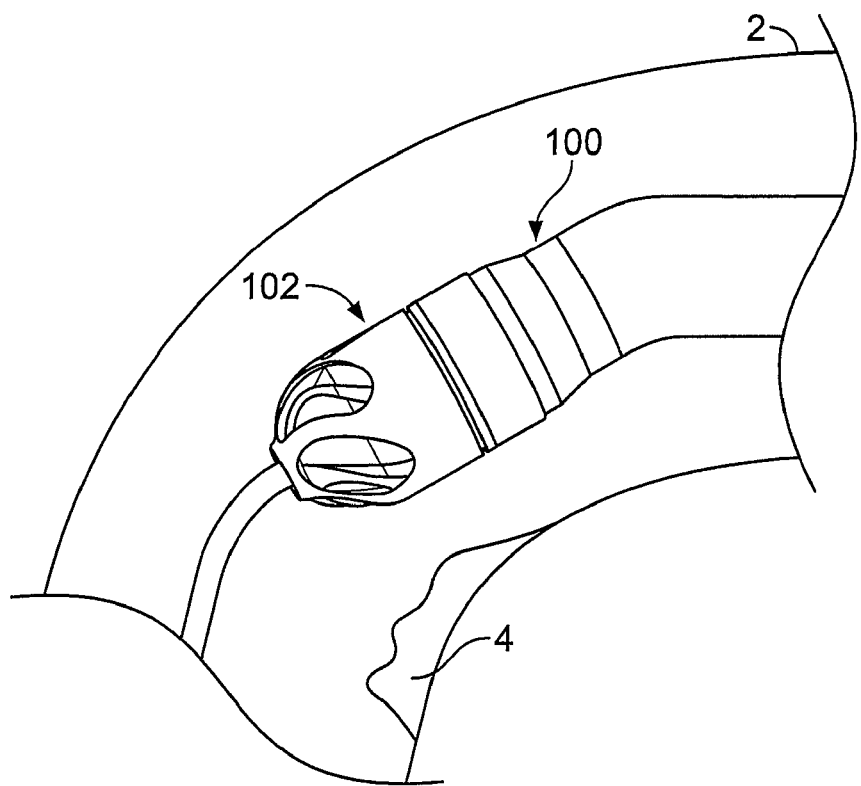
FIG. 6A illustrates articulation of a tip of the device.

FIG. 6A illustrates an example of a variation of a device 100 equipped to have an articulating or steerable cutter assembly 102. The ability to steer the tip of the device 100 is useful under a number of conditions. For example, when debulking an eccentric lesion as shown, the cutting assembly 102 should be pointed towards the side of the vessel 2 having the greater amount of stenotic material 4. Naturally, this orientation helps prevent cutting into the bare wall/vessel 2 and focuses the cutting on stenotic tissue 4. As shown in FIG. 6A when in a curved section of the vessel 2, without the ability to steer, the cutting assembly 102 would tend to bias towards the outside of the curve. Steering allows the cutting assembly 102 to point inward to avoid accidental cutting of vessel wall 2.

Figure 6B:
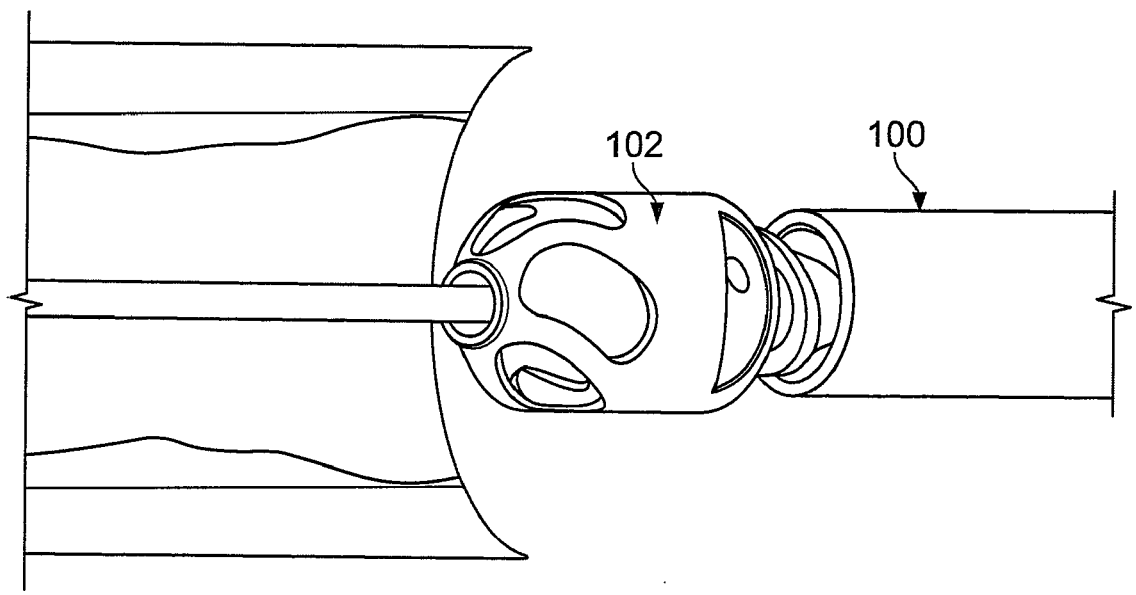
FIG. 6B-6D shows sweeping of the cutting assembly.
Figure 6C:
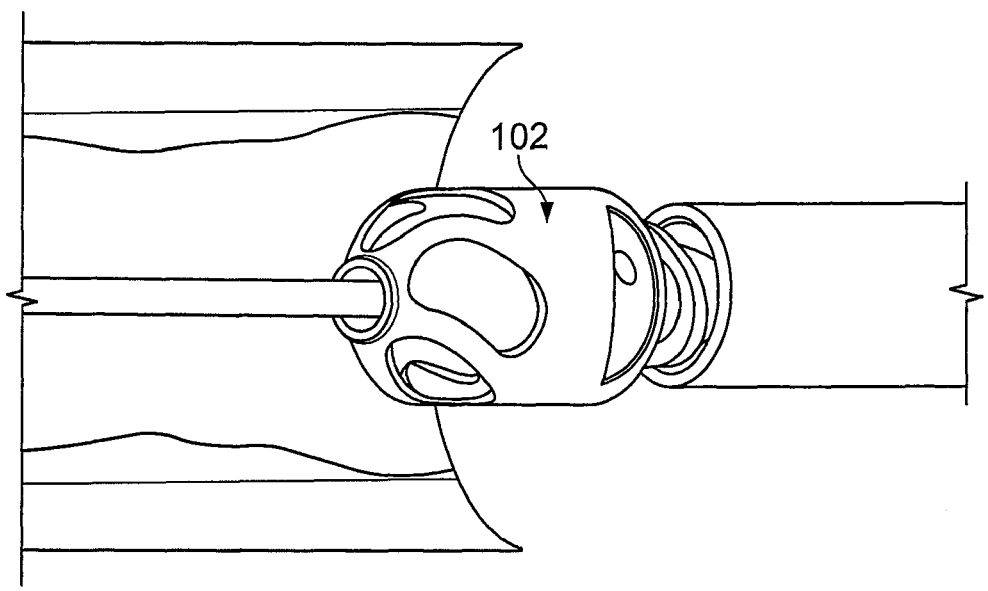
Figure 6D:
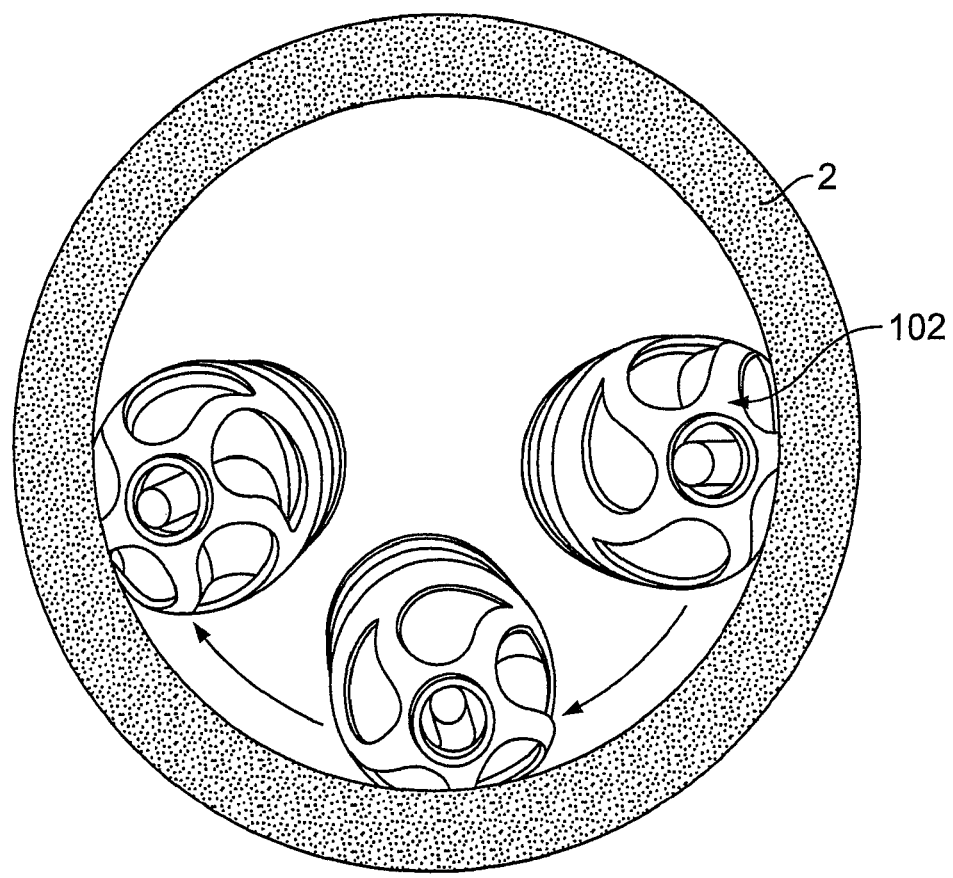

The ability to steer the device 100 also allows for a sweeping motion when cutting occlusive material. FIG. 6B shows the rotation of the cutting assembly 102. As shown in FIG. 6C, when the cutting assembly 102 articulates, rotation of the cutting assembly 102 creates a sweeping motion. FIG. 6D shows a front view taken along an axis of the vessel to illustrate the sweeping motion causing the cutting assembly 102 to "sweep" over a larger region than the diameter of the cutting assembly. In most cases, when articulated, the device will be rotated to sweep over an arc or even a full circle. The rotation of the cutter may or may not be independent of the rotation of the device. A user of the device may couple the sweeping motion of the cutting assembly with axial translation of the catheter for efficient creation of a larger diameter opening over a length of the occluded vessel. The combination of movement can be performed when the device is placed over a guidewire, for example by the use of a lead screw in the proximal handle assembly of the device. In another aspect of the devices described herein, the angle of articulation may be fixed so that the device sweeps in a uniform manner when rotated.

A number of variations to control the deflection of the device 100 are described herein. For example, as shown in FIG. 6 the sheath 122 itself may have a pre-set curve. In such a case, the area of the catheter body 120 adjacent to the cutting assembly 102 will be sufficiently flexible so as to assume the shape of the curved sheath 122.

Figure 6E:
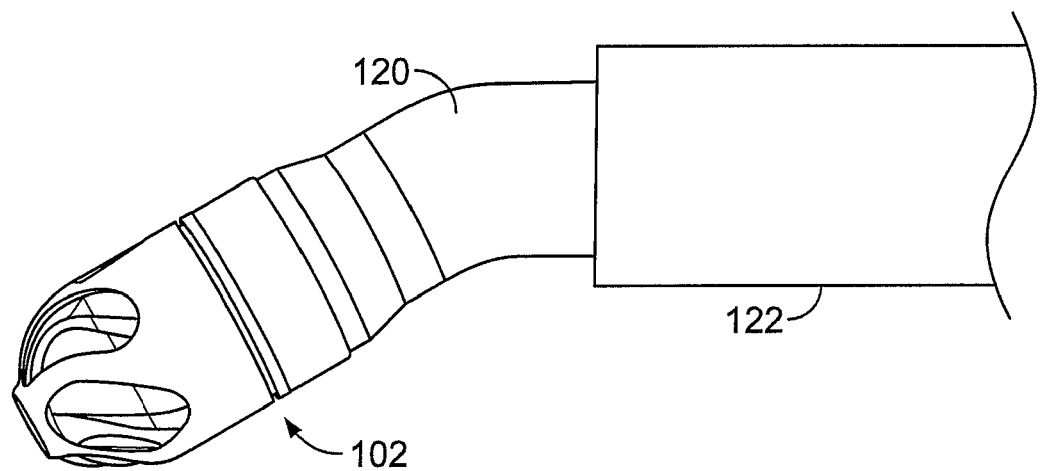
FIG. 6E illustrates another variation where the catheter body includes a set curve in an area that is adjacent to the cutting assembly.

FIG. 6E illustrates another variation where the catheter body 120 includes a set curve in an area that is adjacent to the cutting assembly 102. In this case, the outer sheath 122 can be made to be straight relative to the catheter body 120. Accordingly, advancement of the curved portion of the catheter body 120 out of the sheath 122 causes the catheter body 120 to assume its curved shape. The degree of articulation in such a case may be related to the degree of which the catheter body 120 is advanced out of the sheath 122.

Figure 7:
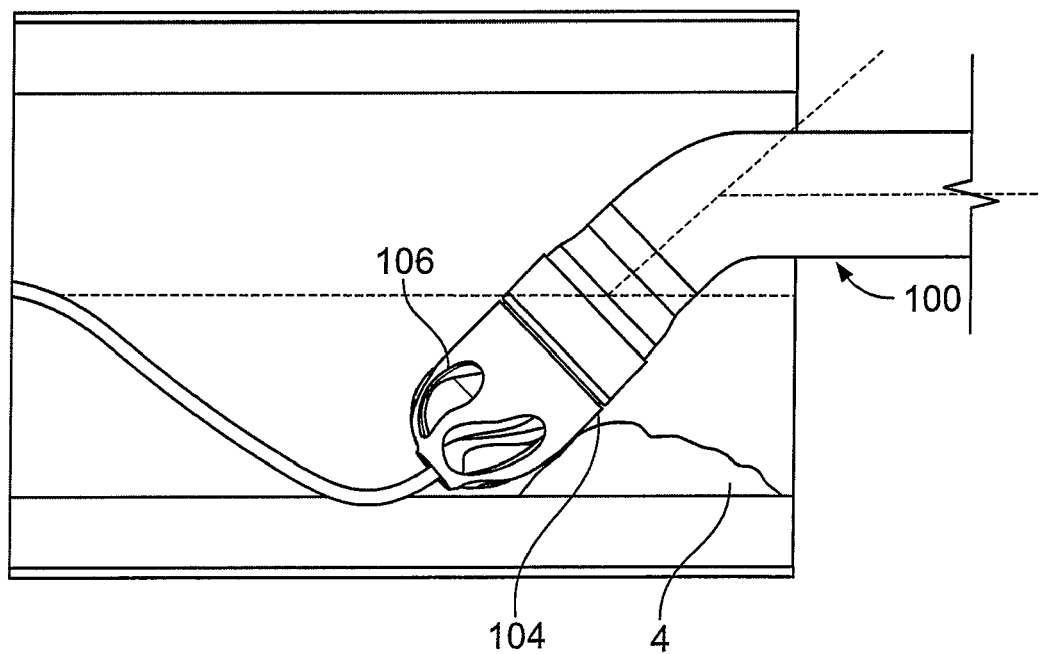
FIG. 7 shows placement of housing windows to prevent damage to the vessel walls.

In addition, the shape of the housing 104 as well as the location of the windows 106 can be chosen so that when the device 100 is substantially aligned with the lesion, or engages it at less than some critical attack angle, it will cut effectively. However, when pivoted at an angle greater than the critical angle, the cutting edges or grinding element will not engage the lesion as shown in FIG. 7. This means that at large deflections, as the catheter tip approaches the vessel wall, it automatically reduces its depth of cut and ultimately will not cut when the critical angle is exceeded. For example, the cutter distal tip is blunt and does not cut. As the catheter tip is deflected outward, the blunt tip contacts the vessel and keeps the cutting edges proximal to the tip from contacting the vessel wall. Also the wire in combination with the device can also act as a buffer to prevent the cutting edges from reaching the vessel.

As mentioned above, variations of the device 100 allow directional control of the cutting assembly 102. In those variations where a slidable, torqueable sheath advances relative to the catheter body 120 (either external or internal to the catheter body) that can be flexed at the distal end. With the sheath flexed the catheter tip is pointed in the direction of the flex and the degree of bias is affected by the amount of flex on the sheath. The sheath can be rotated about the catheter or vessel long axis to change the direction of the cutting assembly. Also as noted above, this rotation can also effect a sweep of the cutting assembly 102 in an arc or a circle larger than a diameter of the cutter 102 (e.g. see FIG. 6D). Such a feature eliminates the need to exchange the device for a separate cutting instrument having a larger cutting head. Not only does such a feature save procedure time, but the device is able to create variable sized openings in body lumens.

Figure 8A:
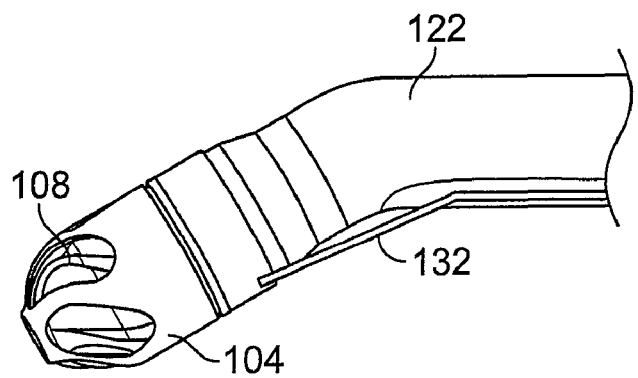
FIGS. 8A-8I show variations of the device for articulating the cutting head.

As shown in FIG. 8A, the tension on a slidable wire 132 in the wall of the sheath 122 can cause flexure of the sheath 122. Compression of the wire can also cause flexure of the sheath in the opposite direction. In one variation, the sheath 122 can be attached to the housing 104 of the cutting assembly 102. Since the housing 104 is rotatable relative to the cutter 108 and the torque shaft 114, the sheath 122 can rotate independently of the torque shaft 114 and cutter 108 to either sweep the cutting assembly 102 or to change direction of the articulated cutting assembly 102 at an independent rate.

Figure 8B:
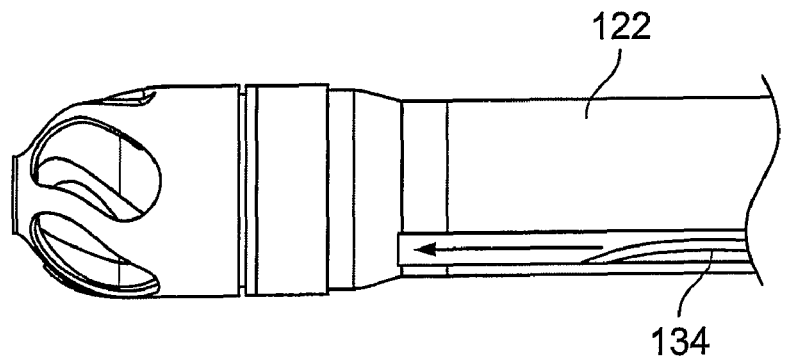
Figure 8C:
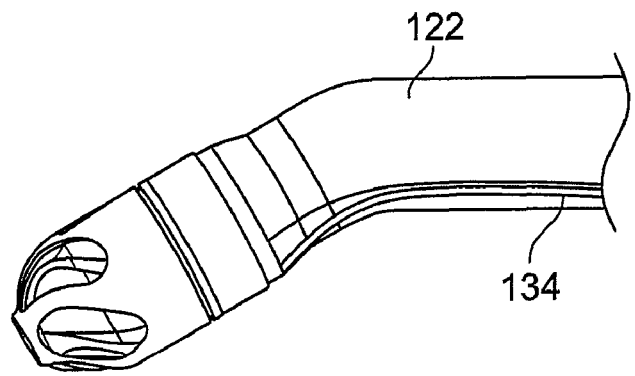
Figure 8D:
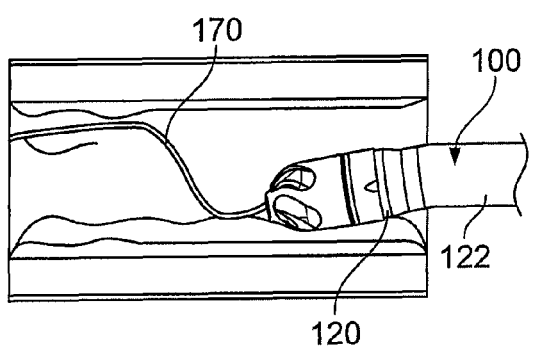
Figure 8E:
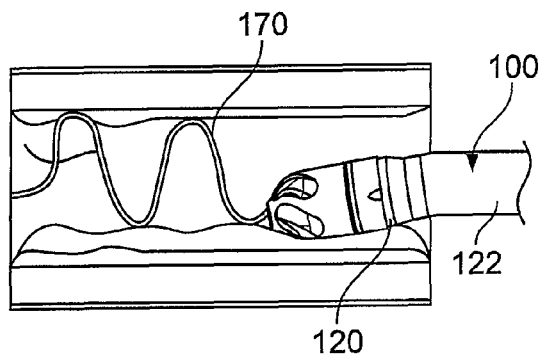
Figure 8F:
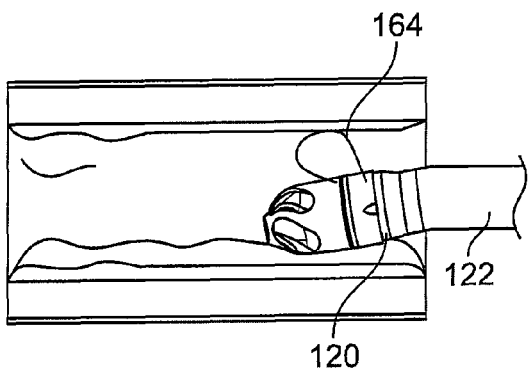
Figure 8G:
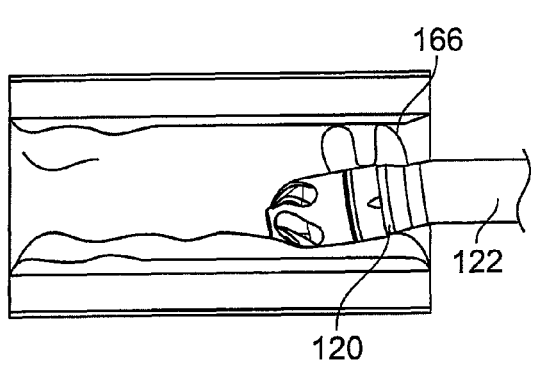
Figure 8H:
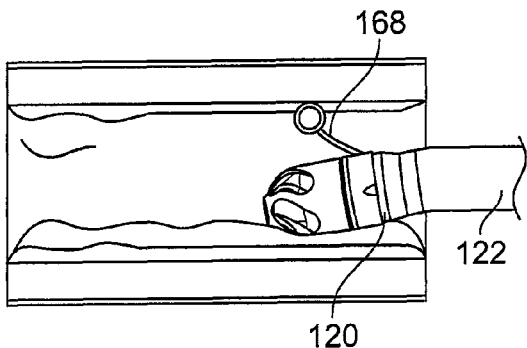
Figure 8I:
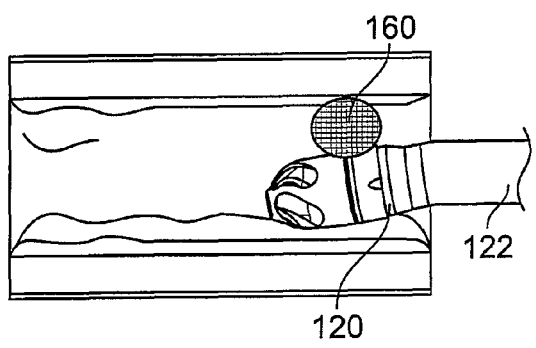

In another variation of the device 100, as shown in FIG. 8B, a preshaped curved wire or mandrel 134 can be advanced in a lumen in either the sheath 122 or catheter 120. As the mandrel 134 advances, the device takes the shape as shown in FIG. 8C. FIGS. 8D-8I illustrate additional mechanisms for flexing the device 100. Such mechanisms can include side balloons 160, meshes, wire loops 164, coils 166, and arms or mandrels 168 and other such structures. These features can be incorporated into catheter body 120 itself or into the sheath 122. If located in the catheter body 120, the entire catheter can be rotated to steer the tip in different directions without necessitating axial advancement of the catheter body 120 in the body lumen. A curved or helical guidewire 170 can also be used to effect the flexion of the catheter tip as shown in FIGS. 8D-8E. The wire can also be actively flexed to control the degree of catheter flexion. All of these deflecting mechanisms can cause the catheter to be deflected in one plane or it can be deflected in three dimensions. The curve on the wire can be in one plane or in 3 dimensions. The sheath can be flexed in one plane or 3 dimensions. Another way to achieve flexion at the distal tip of the catheter is to only partially jacket the distal end with one or more polymers. A bevel at the distal end and/or varying combinations of jacketing and polymers can be used to change the position of the moment arm. This changes the flexibility of the distal end and allows proper deflection.

In addition to providing a means for deflecting the catheter, and allowing the user to sweep the distal tip to engage the lesion as desired, it is also possible to link a separate torque control device to manually or automatically control the sweep of the catheter, independent of the axial control of the catheter insertion and the rotation control of the cutter within the housing. Automatic control may be performed open-loop by user entered settings and activating a switch, or with feedback control designed to further optimize cutting effectiveness, procedural efficiency, and safety. Example structures of how to lock the articulation of the sheath/catheter into place include a lockable collar, a stopper, and friction lock detect mechanisms with one or more springs, coils, or hinges.

Additional components may be incorporated into the devices described herein. For example, it can be desirable to incorporate transducers into the distal region of the catheter to characterize the plaque or to assess plaque and wall thickness and vessel diameter for treatment planning; also transducers may be desired to indicate the progression of debulking or proximity of cutter to vessel wall. For example, pressure sensors mounted on the catheter housing can sense the increase in contact force encountered in the event that the housing is pressed against the vessel wall. Temperature sensors can be used to detect vulnerable plaque. Ultrasound transducers can be used to image luminal area, plaque thickness or volume, and wall thickness. Optical coherence tomography can be used to make plaque and wall thickness measurements. Electrodes can be used for sensing the impedance of contacted tissue, which allows discrimination between types of plaque and also vessel wall. Electrodes can also be used to deliver impulses of energy, for example to assess innervation, to either stimulate or inactivate smooth muscle, or to characterize the plaque (composition, thickness, etc.). For example, transient spasm may be introduced to bring the vessel to a smaller diameter easier to debulk, then reversed either electrically or pharmaceutically. Electrical energy may also be delivered to improve the delivery of drugs or biologic agents, by causing the cell membrane to open in response to the electric stimulation (electroporation). One method of characterization by electrical measurement is electrical impedance tomography.

Figure 9:
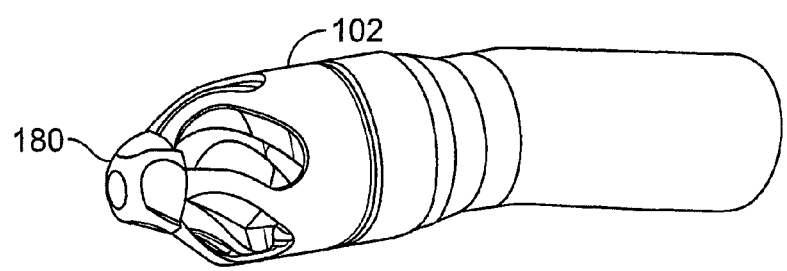
FIG. 9 shows a device with a burr tip.

As shown in FIG. 9, a cutter assembly 102 can also have a burr protruding out its nose. Although the burr 180 may have any type of abrasive surface, in one variation, this burr is blunt and has fine grit (such as diamond grit) to allow for grinding of heavily calcified tissue without injuring adjacent soft tissue. This combination of a burr and cutter allow the distal assembly to remove hard stenotic tissue (calcified plaque) using the burr while the shaving cutter removes softer tissue such as fibrous, fatty tissue, smooth muscle proliferation, or thrombus. In variations, the burr can also have helical flutes to help with aspiration, or the burr can be incorporated to a portion of the cutting edge (for example, the most distal aspect of the cutter).

Figure 10A:
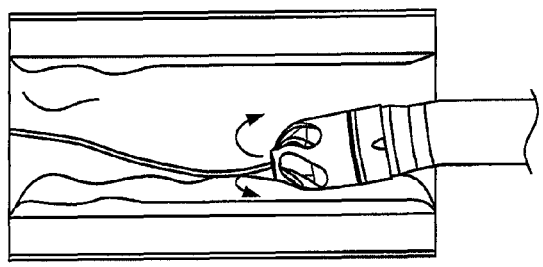
FIGS. 10A-10C provide examples of fluid delivery systems.
Figure 10B:
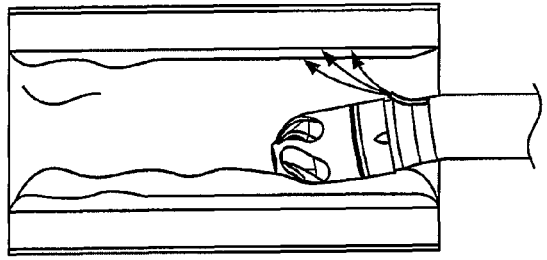
Figure 10C:
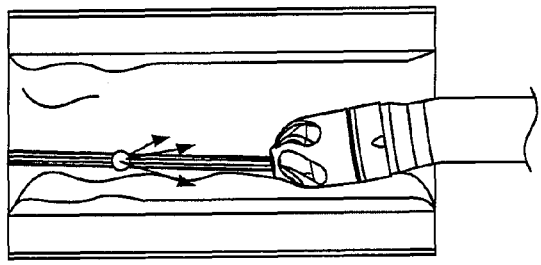

Infusing solutions (flush) into the target treatment site may be desireable. Infused cool saline can prevent heating of blood and other tissue, which reduces the possibility of thrombus or other tissue damage. Heparinized saline can also prevent thrombus and thin out the blood to help maximize effectiveness of aspiration. The flush can also include drugs such as Rapamycin, Paclitaxel or other restenosis-inhibitors. This may help to prevent restenosis and may result in better long term patency. The flush may include paralytics or long-acting smooth muscle relaxants to prevent acute recoil of the vessel. FIGS. 10A-10C illustrate variations of flushing out the device 100. The flush can be infused through the guide wire lumen (FIG. 10A), a side lumen in the catheter shaft (FIG. 10B) or tube, the space between the flexing sheath and the catheter and/or the sideports in the guidwire (FIG. 10C). Flush can come out of a port at the distal end of the cutter head pointing the flush proximally to facility aspiration. Alternatively, by instilling the flush out the distal end of the cutter housing over the rounded surface, the flow may be directed rearward by the Coanda effect. The restenosis-inhibitors can be carried by microcapsules with tissue adhesives or vecro-like features on the surface to stick to inner vessel surface so that the drug adheres to the treatment site, and to provide a time-release controlled by the resorption or dissolving of the coating to further improve efficacy. Such velcro-like features may be constructed with nanoscale structures made of organic or inorganic materials. Reducing the volume of foreign matter and exposing remaining tissue and extracellular matrix to drugs, stimulation, or sensors can make any of these techniques more effective.

Another way to infuse fluid is to supply pressurized fluid at the proximal portion of the guidewire lumen (gravity or pressure feed) intravenous bag, for example. A hemostatic seal with a side branch is useful for this purpose; tuohy-borst adapters are one example of a means to implement this.

Balancing the relative amount of infusion versus fluid volume aspirated allows control over the vessel diameter; aspirating more fluid than is instilled will evacuate the vessel, shrinking its diameter, and allow cutting of lesion at a greater diameter than the atherectomy catheter. This has been a problem for certain open cutter designs that use aspiration, because the aggressive aspiration required to trap the embolic particles evacuates and collapses the artery around the cutter blades; this is both a performance issue because the cutter can bog down from too high torque load, and the cutter can easily perforate the vessel. The shielded design described here obviates both problems, and further requires less aggressive aspiration to be effective, giving a wider range of control to the user.

Figure 11:
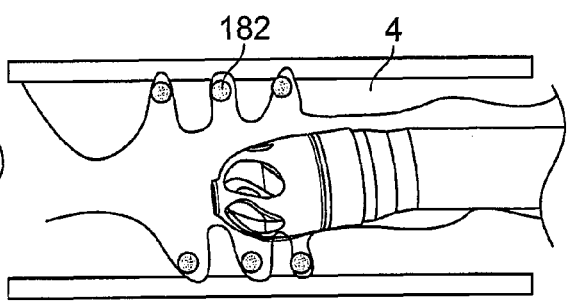
FIG. 11 shows the device placed within a stent or coil.

The devices of the present invention may also be used in conjunction with other structures placed in the body lumens. For example, as shown in FIG. 11, one way to protect the vessel and also allow for maximum plaque volume reduction is to deploy a protective structure such as a thin expandable coil or an expandable mesh 182 within a lesion. As this structure expands after deployment, the thin wire coil or the struts push radially outward through the plaque until it becomes substantially flush with the vessel wall. This expansion of thin members requires minimal displacement of plaque volume and minimizes barotrauma produced in balloon angioplasty or balloon expanded stent delivery. Once the protective structure has expanded fully, atherectomy can be performed to cut away the plaque inside to open up the lumen. The vessel wall is protected by the expanded structure because the structure members (coil or struts) resist cutting by the atherectomy cutter, and are disposed in a way that they cannot invaginate into the cutter housing (and thereby be grabbed by the cutter). It is also possible to adjust the angle of the windows on the atherectomy catheter cutter housing so that they do not align with the struts or coils; the adjustment to orientation may be accounted for in the coil or strut design, in the cutter housing design, or both. Furthermore, the protective member can be relatively flexible and have a low profile (thin elements), so that it may be left in place as a stent. Because the stent in this case relies mainly upon atherectomy to restore lumen patency, it may be designed to exert far less radial force as it is deployed. This allows usage of greater range of materials, some of which may not have as high of stiffness and strength such as bioresorpable polymers. Also, this allows a more resilient design, amenable to the mechanical forces in the peripheral arteries. It also minimizes flow disruption, and may be designed to optimize flow swirl, to minimize hemodynamic complications such as thrombosis related to the relatively low flows found in the periphery. It is also possible to perform atherectomy prior to placing the protective structure, whether or not atherectomy is performed after placing the structure.

Figure 12A:
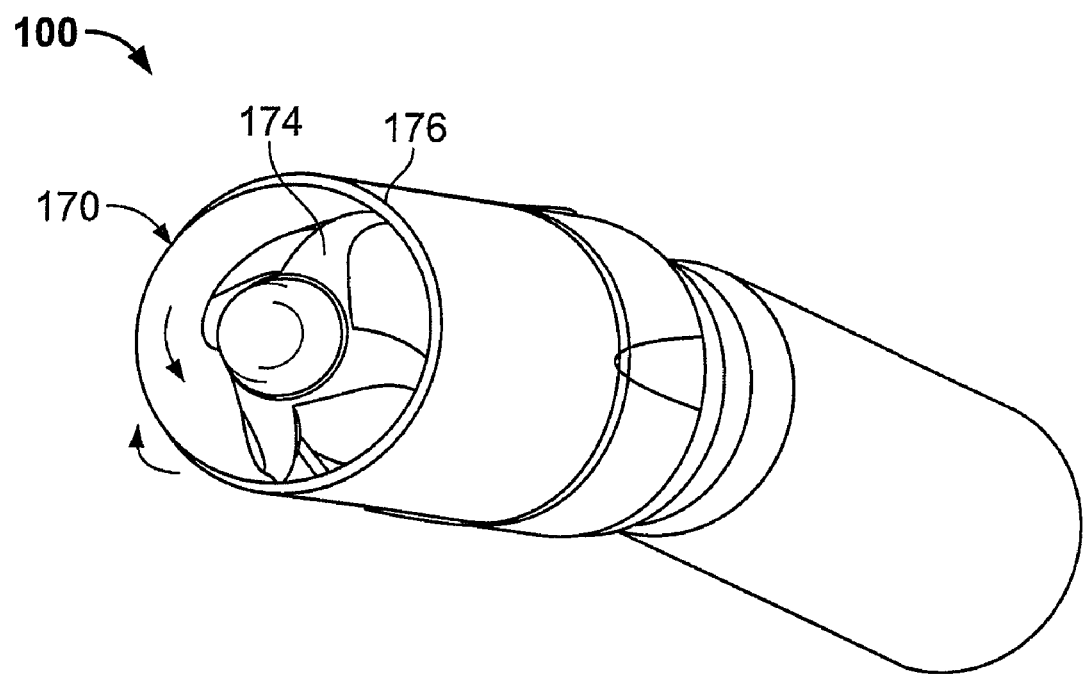
FIGS. 12A-12I show variations of devices.
Figure 12B:
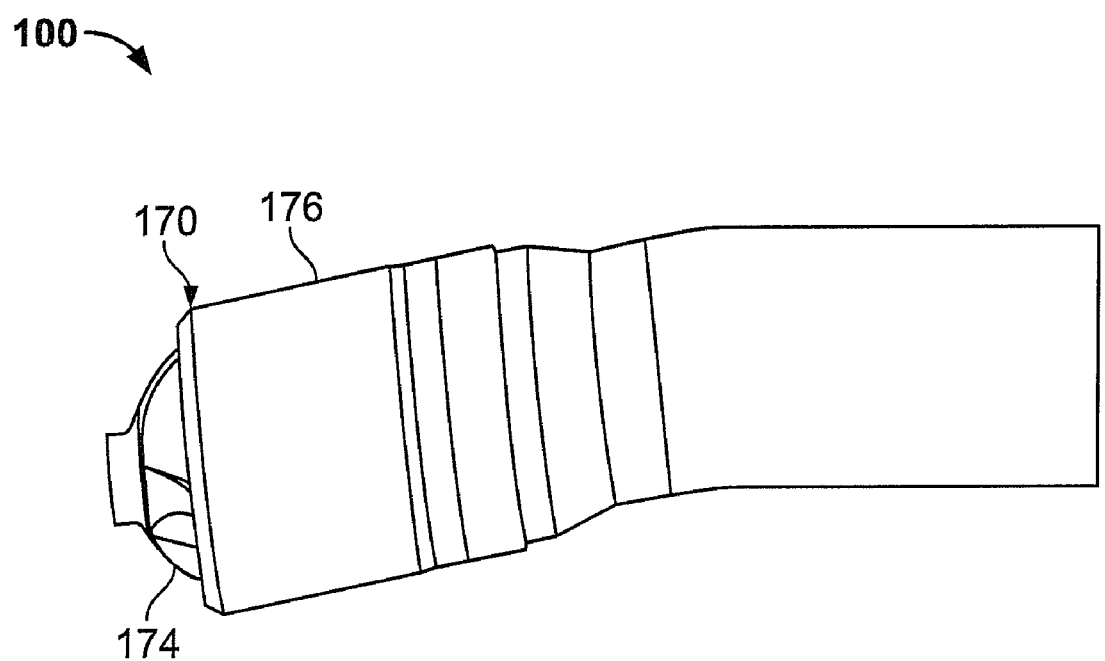
Figure 12C:
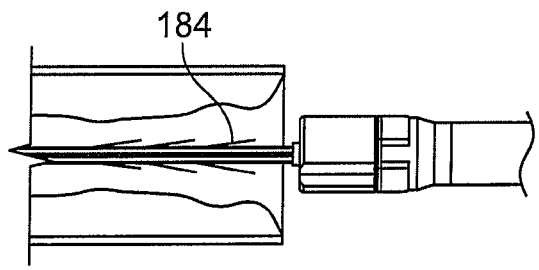
Figure 12D:
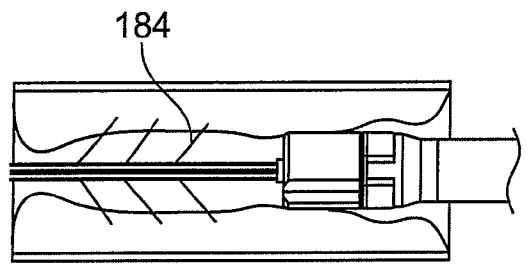
Figure 12E:
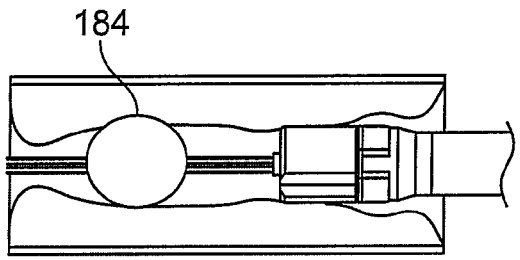
Figure 12F:
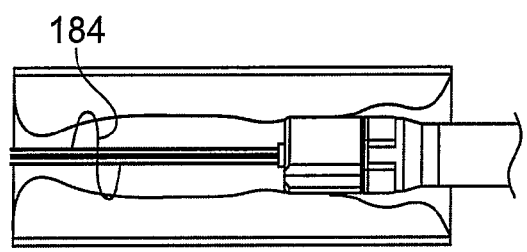
Figure 12G:
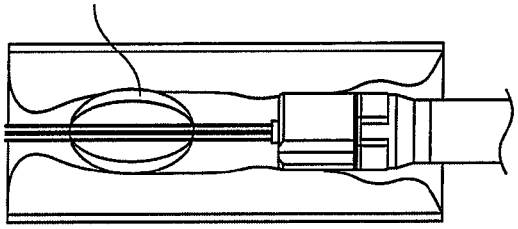
Figure 12H:
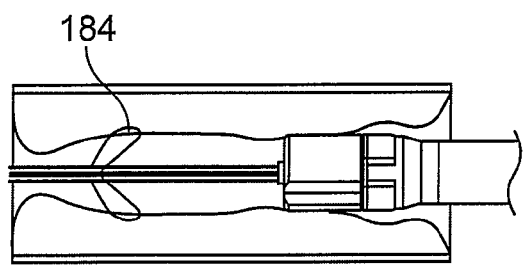
Figure 12I:
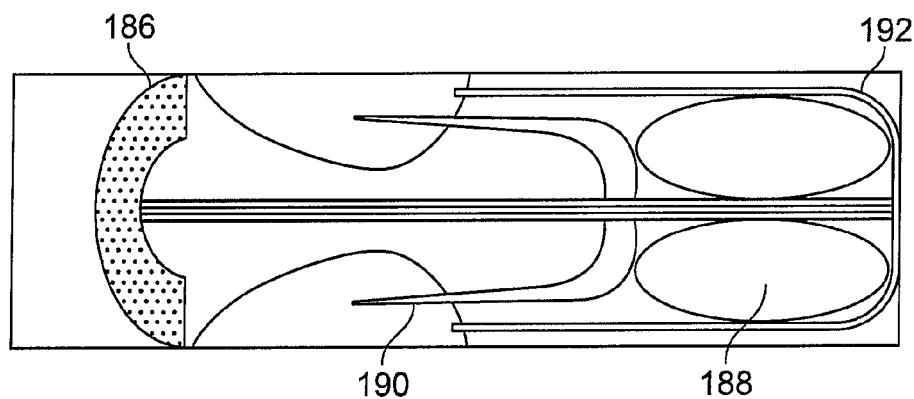

Additional Variations of systems include devices 100 having a cutting assembly 170 comprising spinning turbine-like coring cutter 170 as shown in FIG. 12A. FIG. 12B shows a side view of the coring cutter 170. In use, the coring cutter can be hydraulically pushed to drive the sharp edge through tissue. The turbine like cutters has helical blades 174 on the inside of the sharp cylinder housing 176 (shell). The coring cutter 170 may also have spokes or centering devices 184 as shown to center the shell about the guidewire. This helps to keep the cut of the plaque centered about the vessel wall for safety. The spokes also act as an impeller to pull stenotic tissue back and this helps to drive the cutter forward as well as achieve aspiration to minimize embolization. In the hydraulically driven cutter design, an anchor 186 is deployed in tissue and is connected to a backstop 192. A balloon or hydraulic chamber 188 is then pressurized to expand and pushes the cutting 190 forward through the lesion (See FIG. 12I). One advantage of this approach may be that the technique is similar to angioplasty (which involves pumping up a balloon with an endoflator). One means of anchoring is to use an anchoring guidewire, for example, a guidewire with an inflatable balloon to be placed distal to the atherectomy catheter. Alternatively, the technique of anchoring distally can be used with the previously described torque shaft driven atherectomy catheter.

It is also possible to use the devices and methods described here to restore patency to arterial lesions in the coronary circulation and in the carotid circulation, both by debulking de novo lesions and by debulking in stent restenosis.

The devices and methods described herein also work particularly well in lesions that are challenging to treat with other methods: at bifurcations, in tortuous arteries, and in arteries which are subject to biomechanical stresses (such as in the knee or other joints).

In a further variation of the devices described here, the motor drive unit may be powered by a controller that varies the speed and torque supplied to the catheter to optimize cutting efficiency or to automatically orbit the cutter using variable speed with a fixed flexible distal length of catheter (or providing further orbiting control by controlling the length of the distal flexible section of the catheter).

It is also possible to use feedback control to operate the catheter in a vessel safe mode, so that the rate of cutting is decreased as the vessel wall is approached. This may be accomplished through speed control, or by reducing the degree to which the cutting blades penetrate above the housing window by retracting the cutter axially within the housing. Feedback variables could be by optical (infrared) or ultrasound transducer, or by other transducers (pressure, electrical impedance, etc.), or by monitoring motor performance. Feedback variables may also be used in safety algorithms to stop the cutter, for example in a torque overload situation.

The atherectomy catheter may be further configured with a balloon proximal to the cutter, for adjunctive angioplasty or stent delivery. The catheter may optionally be configured to deliver self-expanding stents. This provides convenience to the user and greater assurance of adjunctive therapy at the intended location where atherectomy was performed.

Further methods include use of similar devices to debulk stenosis in AV hemodialysis access sites (fistulae and synthetic grafts), as well as to remove thrombus. By removing the cutter housing and recessing the fluted cutter within the catheter sheath, a suitable non-cutting thrombectomy catheter may be constructed.

Other methods of use include excising bone, cartilage, connective tissue, or muscle during minimally invasive surgical procedures. For example, a catheter that includes cutting and burr elements may be used to gain access to the spine for performing laminectomy or facetectomy procedures to alleviate spinal stenosis. For this application, the catheter may be further designed to deploy through a rigid cannula over part of its length, or have a rigid portion itself, to aid in surgical insertion and navigation.

For this reason, it is advantageous to couple atherectomy with stenting. By removing material, debulking the lesion, a lesser radial force is required to further open the artery and maintain lumen diameter. The amount of debulking can be tuned to perform well in concert with the mechanical characteristics of the selected stent. For stents that supply greater expansion and radial force, relatively less atherectomy is required for satisfactory result. An alternative treatment approach is to debulk the lesion substantially, which will allow placement of a stent optimized for the mechanical conditions inherent in the peripheral anatomy. In essence, the stent can support itself against the vessel wall and supply mild radial force to preserve luminal patency. The stent may be bioresorbable, and/or drug eluting, with the resorption or elution happening over a period for days to up to 12 weeks or more. A period of 4 to 12 weeks matches well with the time course of remodeling and return to stability as seen in the classic wound healing response, and in particular the known remodeling time course of arteries following stent procedures. In addition, the stent geometry can be optimized to minimize thrombosis by inducing swirl in the blood flow. This has the effect of minimizing or eliminating stagnant or recirculating flow that leads to thrombus formation. Spiral construction of at least the proximal (upstream) portion of the stent will achieve this. It is also beneficial to ensure that flow immediately distal to the stent does not create any stagnant or recirculation zones, and swirl is a way to prevent this also.

Figure 13A:
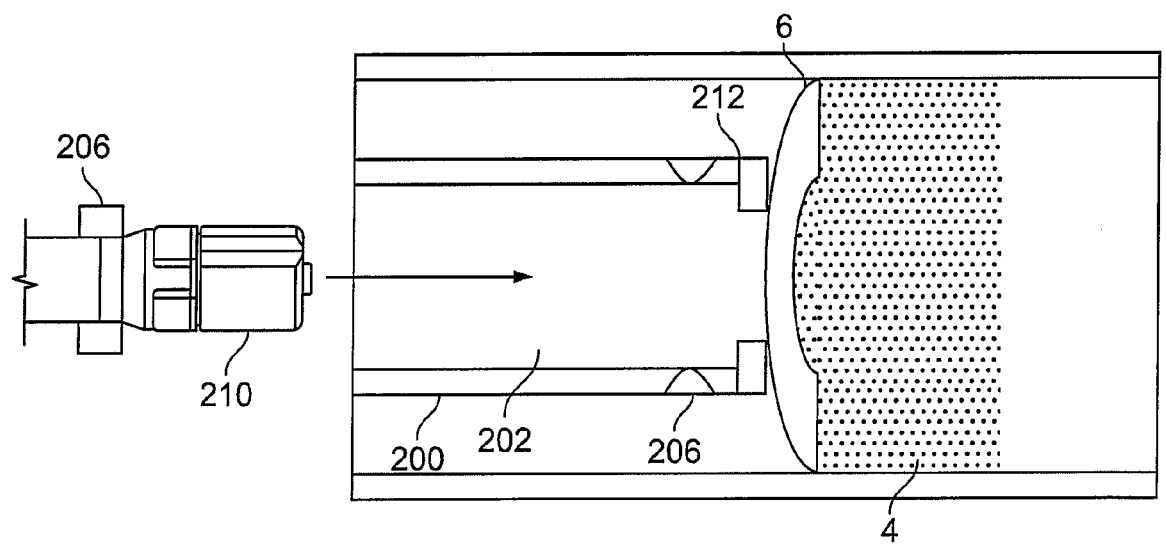
FIGS. 13A-13C show a system for visualizing and crossing total occlusions.
Figure 13B:
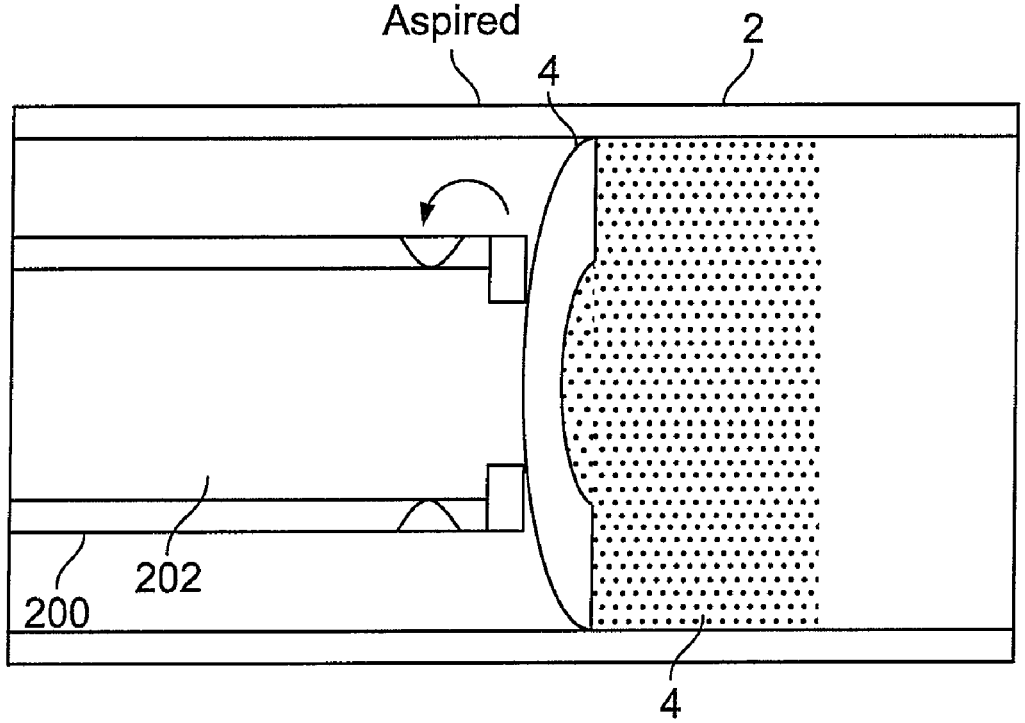
Figure 13C:
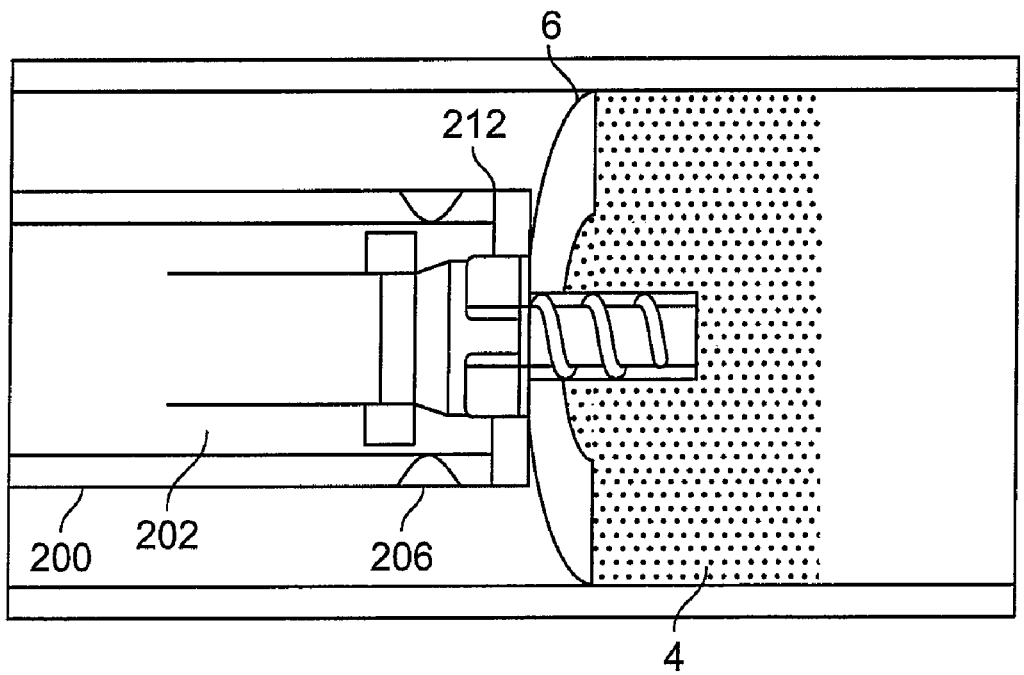

FIG. 13 illustrates another variation of a device for clearing obstructions within body lumens. In some cases where a vessel is totally occluded, a tough fibrous or calcific cap 6 completely or almost completely blocks the lumen. Because of this blockage, fluid cannot flow past the occlusion. This stagnation also makes it difficult or impossible to properly insert a wire across the lesion with an atherectomy device or stiff catheter.

In a typical case of a total occlusion, it is also difficult if not impossible to visualize the lumen near the occlusion because any injected contrast agents cannot flow through the occlusion site.

FIG. 13A shows a system for treating total occlusions. The system can include a support catheter comprising a support tube or catheter 200, having a central lumen 202, the catheter may include side lumens or ports 206, for flush and aspiration. The catheter central lumen 202 can be used to deliver contrast agents 208. In addition, tip centering mechanisms, and an atraumatic tip can be useful. The support catheter can be used with any lumen-creating device 210, such as the devices 100 described above, a laser catheter, an RF probe, or an RF guidewire. When using a coring cutter as shown in FIG. 13, the cutter can have a sharp edge at its tip, helical flutes, helical grooves, or any other mechanism that enables penetration of the fibrous or calcific cap. The cutter and the shaft can be advanced forward within the support catheter, and one or more balloons or baskets can also be deployed by the support catheter to help center it in the vessel.

The lumen-creating device 200 can optionally be made to have a shoulder 212 at its distal end, as shown in FIG. 13A. The shoulder 212 acts as a stop to limit the depth at which the device 200 protrudes beyond the support catheter 200. Such a safety measure may be desired to protect the vessel wall. Driving the device 200 through the tough fibrous cap creates a lumen in the cap. A guidewire may then be placed into the lumen created in the fibrous cap. The coring cutter may be removed with the core.

Next, a guidewire can be used with a cutter assembly to remove some or all of the remaining mass in the vessel. Alternatively, the initial lumen made may be adequately large without further atherectomy. Technical success is typically less than 30 percent or less than 20 percent residual stenosis. Also, balloon angioplasty with or without stenting maybe performed following establishment of a guidewire lumen with a support catheter and a lumen-creating catheter.

Contrast injection and aspiration ports near the distal end of the support circulate contrast agents, enabling the use of fluoroscopy to visualize the lumen adjacent to the total occlusion during diagnosis or treatment. The central lumen 202 of the support catheter 200 can also be used to inject or aspire the contrast agents 208. The contrast agents can circulate through the center lumen 202 in the support catheter 200 and at least one port 206 in various configurations. The fluid can circulate about the distal tip of the catheter, the motion of the fluid being circular as shown in FIG. 13B. For example, the fluid can be injected through the central lumen 202, travel around the distal tip, and then is aspirated back into the support catheter through ports 206 on the side of the surface of the support catheter 200. To illustrate another possible configuration, the fluid can be ejected through the side ports, and then aspired through the central lumen. This recirculation of the contrast agent permits imaging of the vessel at the site of the occlusion.

It is noted that the descriptions above are intended to provide exemplary embodiments of the devices and methods. It is understood that, the invention includes combinations of aspects of embodiments or combinations of the embodiments themselves. Such variations and combinations are within the scope of this disclosure.

We claim:

1. A method for cutting and removing occlusive material from a body lumen, the method comprising:
providing a vascular device comprising
a catheter body sized and configured for axial advancement in the body lumen, the catheter body having a center axis along which axial advancement occurs and including spaced apart proximal and distal ends,
a cutter assembly having an outside diameter attached at the distal end of the catheter body, the cutter assembly comprising a housing having at least one opening and a cutter having at least one helical cutting surface configured to rotate about the center axis relative to the housing to cut occlusive material at the distal end of the catheter body and convey the occlusive material from the body lumen proximally into the housing,
a drive mechanism at the proximal end of the catheter body;
a torque shaft coupled to the drive mechanism and extending through the catheter body and coupled to the cutter to rotate the helical cutting blade about the center axis relative to the housing,
a conveyor mechanism helically wound about the torque shaft in a direction common with the helical cutting blade to convey the occlusive material conveyed into the housing by the helical cutting blade further proximally along the catheter body for discharge without supplement of a vacuum pump, and
a deflecting mechanism slidable within the catheter body in response to a force applied at the proximal end of the catheter body for deflecting the cutter assembly relative to the center axis of the catheter body to point the cutter assembly toward a side of the body lumen without necessitating axial advancement of the catheter body in the body lumen, manipulating the proximal end of the catheter body to insert the distal end of the catheter body within the body lumen, manipulating the proximal end of the catheter body to advance the distal end of the catheter body within the body lumen toward the occlusive material, operating the drive mechanism to rotate the helical cutting surface about the central axis to cut occlusive material at the distal end of the catheter body, to convey the occlusive material from the body lumen proximally into the housing, and to convey the occlusive material conveyed into the housing by the helical cutting surface further proximally along the catheter body by the conveyor mechanism for discharge without supplement of a vacuum pump, operating the deflecting mechanism at the proximal end of the catheter body to deflect the cutter assembly relative to the center axis of the catheter body to point the cutter assembly toward a side of the body lumen without necessitating axial advancement of the catheter body in the body lumen, and rotating the distal end of the catheter body when the cutter assembly is deflected to sweep the cutter assembly in an arc about the center axis to cut occlusive material in a region larger than the outside diameter of the cutter assembly, wherein rotating the distal end of the catheter body comprises operating a torque control device separate from the deflecting mechanism to manually or automatically control the sweep of the cutter assembly.

2. A method according to claim 1 wherein manipulating the proximal end of the catheter body to advance the distal end of the catheter body within the body lumen toward the occlusive material includes advancing the distal end of the catheter body within a body lumen having a bifurcation.

3. A method according to claim 1 wherein manipulating the proximal end of the catheter body to advance the distal end of the catheter body within the body lumen toward the occlusive material includes advancing the distal end of the catheter body within a tortuous body lumen.

4. A method according to claim 1 wherein manipulating the proximal end of the catheter body to advance the distal end of the catheter body within the body lumen toward the occlusive material includes advancing the distal end of the catheter body within a body lumen subject to biomechanical stresses.

5. A method according to claim 1 wherein operating the drive mechanism to rotate the helical cutting blade about the central axis to cut and convey the occlusive material from the body lumen includes restoring patency to a lesion in the body lumen.

6. A method according to claim 1 wherein operating the drive mechanism to rotate the helical cutting blade about the central axis to cut and convey the occlusive material from the body lumen comprises debulking a lesion in the body lumen.

* * * * *